United States Patent
Chodorowski-Kimmes

(10) Patent No.: US 10,874,602 B2
(45) Date of Patent: Dec. 29, 2020

(54) HAIR DYEING PROCESS COMPRISING A PHOSPHONIC ETHYLENIC POLYMER AND A PIGMENT

(71) Applicant: L'OREAL, Paris (FR)

(72) Inventor: Sandrine Chodorowski-Kimmes, Aulnay-sous-Bois (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/500,615

(22) PCT Filed: Apr. 9, 2018

(86) PCT No.: PCT/EP2018/059029
§ 371 (c)(1),
(2) Date: Oct. 3, 2019

(87) PCT Pub. No.: WO2018/185337
PCT Pub. Date: Oct. 11, 2018

(65) Prior Publication Data
US 2020/0188282 A1  Jun. 18, 2020

(30) Foreign Application Priority Data

Apr. 7, 2017  (FR) .................... 17 53070

(51) Int. Cl.
*A61Q 5/10* (2006.01)
*A61K 8/81* (2006.01)
*A61K 8/25* (2006.01)
*A61Q 5/06* (2006.01)

(52) U.S. Cl.
CPC ............. *A61K 8/8152* (2013.01); *A61K 8/25* (2013.01); *A61Q 5/065* (2013.01); *A61K 2800/43* (2013.01); *A61K 2800/87* (2013.01)

(58) Field of Classification Search
CPC ........ A61Q 5/065; A61K 8/8152; A61K 8/25; A61K 8/55; A61K 8/89; A61K 8/24; A61K 2800/43; A61K 2800/594; A61K 2800/87
USPC ...................................... 8/405, 584
See application file for complete search history.

(56) References Cited

U.S. PATENT DOCUMENTS 6,106,577 A * 8/2000 Audousset ........... A61K 8/8147
8/403
2017/0252283 A1* 9/2017 Lion ..................... A61K 8/898

FOREIGN PATENT DOCUMENTS

FR    2 741 530 A1   5/1997
FR    3 022 909 A1   1/2016
WO    WO 2017/108599 A1   6/2017

OTHER PUBLICATIONS

STIC Search Report dated May 28, 2020.*
International Search Report dated Jun. 18, 2018 in PCT/EP2018/059029 filed Apr. 9, 2018.

* cited by examiner

*Primary Examiner* — Eisa B Elhilo
(74) *Attorney, Agent, or Firm* — Oblon, McClelland, Maier & Neustadt, L.L.P.

(57) ABSTRACT

Hair dyeing process comprising a phosphonic ethylenic polymer and a pigment The invention relates to a process for dyeing hair comprising at least one pigment and at least one phosphonic polymer derived from the polymerization of: (a) 45% to 95% by weight of ethylenic monomer bearing an at least $C_8$ linear or branched alkyl group; (b) 5% to 25% by weight of vinylphosphonic acid monomer; (c) 0 to 50% by weight of additional monomer chosen from: (i) linear or branched $C_1$-$C_6$ alkyl (meth)acrylate or $C_6$-$C_{12}$ cycloalkyl (meth)acrylate non-silicone monomers; (ii) specific polydimethylsiloxane silicone monomers bearing a mono(meth)acryloyloxy end group.

35 Claims, No Drawings

HAIR DYEING PROCESS COMPRISING A PHOSPHONIC ETHYLENIC POLYMER AND A PIGMENT

The present invention relates to a process for dyeing hair using a pigment and an ethylenic polymer bearing a phosphonic acid group.

In the field of dyeing of keratin fibres, it is already known practice to dye keratin fibres via various techniques using direct dyes for non-permanent dyeing or dye precursors for permanent dyeing.

Non-permanent dyeing or direct dyeing consists in dyeing keratin fibres with dye compositions containing direct dyes. These dyes are coloured and colouring molecules that have affinity for keratin fibres. They are applied to the keratin fibres for the time required to obtain the desired colouring, and are then rinsed out.

The standard dyes that are used are, in particular, dyes of the nitrobenzene, anthraquinone, nitropyridine, azo, xanthene, acridine, azine or triarylmethane type, or natural dyes.

Some of these dyes may be used under lightening conditions, which enables the production of colourings that are visible on dark hair.

It is also known practice to dye keratin fibres permanently via oxidation dyeing. This dyeing technique consists in applying to the keratin fibres a composition containing dye precursors such as oxidation bases and couplers. These precursors, under the action of an oxidizing agent, form one or more coloured substances in the hair.

The variety of molecules used as oxidation bases and couplers allows a wide range of colours to be obtained, and the colourings resulting therefrom are generally permanent, strong and resistant to external agents, especially to light, bad weather, washing, perspiration and rubbing.

In order to be visible on dark hair, these two dyeing techniques require prior or simultaneous bleaching of the keratin fibres. This bleaching step, performed with an oxidizing agent such as hydrogen peroxide or persalts, results in appreciable degradation of the keratin fibres, which impairs their cosmetic properties. The hair then has a tendency to become coarse, more difficult to disentangle and more brittle.

Another dyeing method consists in using pigments. Specifically, the use of pigment at the surface of the keratin fibres generally makes it possible to obtain visible colorations on dark hair, since the surface pigment masks the natural colour of the fibre. The use of pigment for dyeing keratin fibres is described, for example, in patent application FR 2 741 530, which recommends using for the temporary dyeing of keratin fibres a composition comprising at least one dispersion of film-forming polymer particles comprising at least one acid function and at least one pigment dispersed in the continuous phase of said dispersion.

The colourings obtained via this dyeing method have the drawback of being removed from the very first shampoo wash.

It is moreover known practice from patent application FR 2 907 678 to perform coloured coating of the hair using a composition comprising a polysiloxane/polyurea block copolymer and a pigment. However, with such a composition, the coatings obtained are not always very homogeneous and the individualization of the hair strands is not always very good.

It is also known practice from patent EP 1 392 222 to use a cosmetic composition for caring for and/or treating keratin materials, comprising a supramolecular polymer bearing a polymer backbone and at least two groups that are capable of forming at least three hydrogen bonds, and from patent EP 1 435 900 to use a hair composition comprising a supramolecular polymer comprising a polymer backbone and at least two groups that are capable of forming at least three hydrogen bonds and a surfactant or hair-conditioning agent. Thus, the aim of the present invention is to provide a composition for dyeing keratin fibres, such as the hair, which can produce coloured coatings that show good resistance to attacking factors such as brushing, do not leach, are resistant to sweat, light and bad weather, and are persistent with respect to shampooing and the various attacking factors to which the hair may be subjected, without degradation of the keratin fibres and while at the same time conserving perfectly individualized hair strands.

One subject of the present invention is a hair dyeing process which comprises the application to the hair of at least one pigment and of at least one phosphonic polymer, the phosphonic polymer being derived from the polymerization of:
 (a) 25% to 95% by weight, relative to the total weight of monomers, of an ethylene monomer bearing an at least 08 linear or branched alkyl group;
 (b) 5% to 25% by weight of vinylphosphonic acid monomer of formula (I) defined below;
 (c) 0 to 50% by weight of additional monomer chosen from:
  (i) linear or branched $C_1$-$C_6$ alkyl (meth)acrylate or $C_6$-$C_{12}$ cycloalkyl (meth)acrylate non-silicone monomers;
  (ii) polydimethylsiloxane silicone monomers bearing a mono(meth)acryloyloxy end group as defined below;
 the composition(s) used being anhydrous when the additional component is an amino alkoxysilane.

Such an ethylene polymer is referred to hereinbelow as a phosphonic polymer.

A subject of the invention is also a composition comprising, at least one pigment and at least one phosphonic polymer as described previously.

According to a first embodiment of the process according to the invention, a composition derived from the mixing (extemporaneous) of a composition comprising a phosphonic polymer as described previously and an additional component as defined previously, or a composition containing said additional component, is applied to the hair, the composition derived from the mixing being anhydrous when the additional component is an amino alkoxysilane, and the applied composition comprising at least one pigment.

According to one embodiment of the process according to the invention, the mixing of the composition comprising the phosphonic polymer, a pigment and of the additional component, or of the composition containing said additional component, is performed in a time of between 1 minute and 24 hours before its application to keratin fibres, and preferably between 5 and 30 minutes.

According to a second embodiment of the process according to the invention, an additional component as defined below, or a composition containing said additional component and a composition comprising a phosphonic polymer as described previously, are applied sequentially to the hair, the compositions used being anhydrous when the additional component is an amino alkoxysilane, and at least one of the applied compositions comprising at least one pigment.

According to one embodiment of the process according to the invention, the composition comprising the phosphonic polymer is first applied to the hair, and said additional component or a composition containing same and comprising a physiologically acceptable medium is then applied, one and/or the other of the compositions comprising at least one pigment. According to another embodiment, the pigment is applied using a separate composition.

According to another embodiment, said additional component, or a composition containing same and comprising a physiologically acceptable medium, is applied first to the hair, and the composition comprising the phosphonic polymer is then applied, one and/or the other of the compositions comprising at least one pigment. According to another embodiment, the pigment is applied using a separate composition.

A subject of the invention is also a composition obtained by mixing a phosphonic polymer as described previously or a composition containing same, and an additional component as defined below or a composition, the composition being anhydrous when the additional compound is an amino alkoxysilane, one and/or the other of the compositions comprising at least one pigment. According to another embodiment, the pigment is applied using a separate composition.

A subject of the invention is also a kit comprising a first composition comprising said phosphonic polymer as described previously and a second composition comprising an additional component as defined below, the first and/or second compositions comprising at least one pigment, and the compositions each being packaged in a separate packaging assembly, the compositions being anhydrous when the additional compound is an amino alkoxysilane.

The composition packaging assembly is, in a known manner, any packaging that is suitable for storing cosmetic compositions (in particular a bottle, tube, spray bottle or aerosol bottle). Such a kit allows the process for treating keratin materials according to the invention to be performed.

The phosphonic polymer used according to the invention is an ethylene polymer derived from the polymerization of:
(a) 45% to 95% by weight, relative to the total weight of monomers, of an ethylene monomer bearing an at least $C_8$ linear or branched alkyl group;
(b) 5% to 25% by weight of vinylphosphonic acid monomer of formula (I) defined below;
(c) 0 to 50% by weight of additional monomer chosen from:
  (i) linear or branched $C_1$-$C_6$ alkyl (meth)acrylate or $C_6$-$C_{12}$ cycloalkyl (meth)acrylate non-silicone monomers;
  (ii) polydimethylsiloxane silicone monomers bearing a mono(meth)acryloyloxy end group as defined below;

The phosphonic polymer used according to the invention comprises an ethylenic monomer bearing an at least $C_8$ linear or branched alkyl group (referred to as a fatty-chain ethylenic monomer); said alkyl group may be a linear or branched $C_8$-$C_{22}$ or $C_8$ to $C_{12}$ alkyl group.

Such a fatty-chain ethylenic monomer may be chosen from:
a) linear or branched $C_8$-$C_{22}$ alkyl (meth)acrylates (i.e. comprising a $C_8$-$C_{22}$ alkyl group);
b) the (meth)acrylamides of formula $CH_2=C(R_1)=CONR_3R_4$ in which $R_1$ represents a hydrogen atom or a methyl radical, $R_3$ represents a hydrogen atom or a linear or branched $C_1$-$C_{12}$ alkyl group, and $R_4$ represents a linear or branched $C_8$ to $C_{12}$ alkyl group, such as an isooctyl, isononyl or undecyl group;
c) the vinyl esters of formula $R_5$—CO—O—CH=$CH_2$ in which $R_5$ represents a linear or branched $C_8$-$C_{22}$ alkyl group;
d) the ethers of formula $R_6$—O—CH=$CH_2$ in which $R_6$ represents a linear or branched $C_8$-$C_{22}$ alkyl group.

Linear or branched $C_8$-$C_{22}$ alkyl groups that may be mentioned include octyl, 2-ethylhexyl, isooctyl, nonyl, decyl, undecyl, lauryl, myristyl, palmityl, stearyl, eicosyl and behenyl, and especially a 2-ethylhexyl, lauryl, behenyl or stearyl group.

Preferably, the fatty-chain ethylenic monomer is chosen from linear or branched $C_8$-$C_{22}$ alkyl (meth)acrylates, for instance 2-ethylhexyl acrylate, 2-ethylhexyl methacrylate, lauryl acrylate, lauryl methacrylate, behenyl acrylate, behenyl methacrylate, stearyl acrylate and stearyl methacrylate.

2-Ethylhexyl acrylate, stearyl acrylate or stearyl methacrylate is preferably used.

2-Ethylhexyl acrylate is preferentially used.

The fatty-chain monomer may be present in said ethylenic polymer in a content ranging from 45% to 95% by weight and preferably ranging from 55% to 95% by weight, relative to the total weight of monomers.

In the absence of additional monomer in the ethylenic polymer, the fatty-chain monomer may be present in a content ranging from 75% to 95% by weight, preferably ranging from 85% to 95% by weight and preferentially ranging from 87% to 93% by weight, relative to the total weight of monomers.

In the presence of additional monomer in the phosphonic polymer, the fatty-chain monomer may be present in a content ranging from 45% to 94.5% by weight, preferably ranging from 45% to 90% by weight, preferentially ranging from 55% to 80% by weight and more preferentially ranging from 58% to 73% by weight, relative to the total weight of monomers.

The vinylphosphonic acid monomer corresponds to the following formula (I):

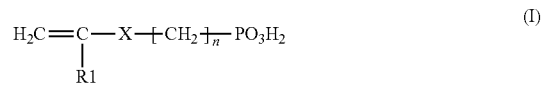

in which:
R1 denotes H or —$CH_3$;
X denotes a covalent bond and n denotes an integer ranging from 0 to 14;
or X denotes a —COO— group and n denotes an integer ranging from 2 to 6.

Advantageously, for the monomer of formula (I), X denotes a covalent bond and n is an integer ranging from 0 to 6 or X denotes a —COO— group and n is an integer ranging from 2 to 4.

Preferably, for the monomer of formula (I):

R1=H

X denotes a covalent bond and n denotes an integer ranging from 0 to 4.

As examples of monomers of formula (I), mention may be made of:
vinylphosphonic acid;
3-butenylphosphonic acid;
4-pentenylphosphonic acid;
10-undecenylphosphonic acid;
11-dodecenylphosphonic acid;
2-phosphonoethyl ester of 2-propenoic acid;
2-phosphonoethyl ester of 2-methyl-2-propenoic acid.
Preferably, monomer (I) is vinylphosphonic acid.
The vinylphosphonic acid monomer (I) may be present in said phosphonic polymer in a content ranging from 5% to 15% by weight and preferably ranging from 7% to 13% by weight, relative to the total weight of monomers.

The additional non-silicone monomer chosen from linear or branched $C_1$-$C_6$ alkyl (meth) acrylates may be, for example, methyl (meth)acrylate, ethyl (meth)acrylate, propyl (meth)acrylate, n-butyl (meth)acrylate, isobutyl (meth)acrylate, pentyl (meth)acrylate or hexyl (meth)acrylate.

The $C_6$-$C_{12}$ cycloalkyl (meth)acrylate is preferably isobornyl (meth)acrylate.

The additional non-silicone monomer may be present in said phosphonic polymer in a content ranging from 0.5% to 50% by weight, relative to the total weight of monomers, preferably ranging from 5% to 50% by weight, preferentially ranging from 15% to 40% by weight and more preferentially ranging from 20% to 35% by weight.

The additional silicone monomer is a polydimethylsiloxane bearing a mono(meth)acryloyloxy end group of formula (II) (referred to hereinbelow as a silicone monomer) below:

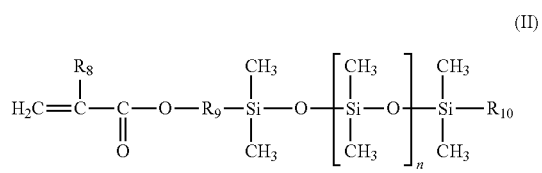

(II)

in which:
- $R_8$ denotes a hydrogen atom or a methyl group; preferably methyl;
- $R_9$ denotes a linear or branched, preferably linear, divalent hydrocarbon-based group containing from 1 to 10 carbon atoms, preferably containing from 2 to 4 carbon atoms, and optionally containing one or two —O— ether bonds; preferably an ethylene, propylene or butylene group;
- $R_{10}$ denotes a linear or branched alkyl group containing from 1 to 10 carbon atoms, especially from 2 to 8 carbon atoms; preferably methyl, ethyl, propyl, butyl or pentyl;
- n denotes an integer ranging from 1 to 300, preferably ranging from 3 to 200 and preferentially ranging from 5 to 100.

Use may be made in particular of monomethacryloyloxypropyl polydimethylsiloxanes such as those sold under the names MCR-M07, MCR-M17, MCR-M11 and MCR-M22 by Gelest Inc or the silicone macromonomers sold under the names X-22-2475, X-22-2426 and X-22-174DX by Shin-Etsu.

The additional silicone monomer (II) may be present in said phosphonic polymer in a content ranging from 5% to 50% by weight, relative to the total weight of monomers, preferably ranging from 15% to 40% by weight, preferentially ranging from 20% to 35% by weight and especially ranging from 25% to 35% by weight.

According to one embodiment of the invention, the phosphonic polymer does not comprise any additional monomer: it is formed from ethylenic monomer bearing an at least $C_8$ linear or branched alkyl group and maleic anhydride.

According to another embodiment of the invention, the phosphonic polymer comprises at least one additional monomer as defined previously. The additional monomer may be present in said phosphonic polymer in a content ranging from 5% to 50% by weight, relative to the total weight of monomers, preferably ranging from 15% to 40% by weight, preferentially ranging from 20% to 35% by weight and especially ranging from 25% to 35% by weight.

According to another embodiment of the invention, the phosphonic polymer comprises at least one additional non-silicone monomer as defined previously. Preferably, it is a $C_6$-$C_{12}$ cycloalkyl (meth)acrylate.

According to another embodiment of the invention, the phosphonic polymer comprises at least one additional silicone monomer as defined previously.

According to another embodiment of the invention, the phosphonic polymer comprises at least one additional non-silicone monomer and at least one additional silicone monomer as defined previously.

According to a first embodiment of the invention, the phosphonic polymer comprises, or consists of:
(a) 75% to 95% by weight, relative to the total weight of monomers, of linear or branched $C_8$-$C_{22}$ alkyl (meth)acrylate;
(b) 5% to 25% by weight of vinylphosphonic acid monomer of formula (I) as defined previously.

The phosphonic polymer especially comprises, or consists of:
(a) 75% to 95% by weight, relative to the total weight of monomers, of linear or branched $C_8$-$C_{18}$ alkyl (meth)acrylate;
(b) 5% to 25% by weight of vinylphosphonic acid monomer of formula (I) as defined previously.

In particular, the phosphonic polymer comprises, or consists of:
(a) 75% to 95% by weight, relative to the total weight of monomers, of 2-ethylhexyl (meth)acrylate;
(b) 5% to 25% by weight of vinylphosphonic acid.

In particular, the phosphonic polymer comprises, or consists of:
(a) 75% to 95% by weight, relative to the total weight of monomers, of stearyl (meth)acrylate;
(b) 5% to 25% by weight of vinylphosphonic acid.

In particular, the phosphonic polymer comprises, or consists of:
(a) 75% to 95% by weight, relative to the total weight of monomers, of a mixture of 2-ethylhexyl (meth)acrylate and of stearyl (meth)acrylate;
(b) 5% to 25% by weight of vinylphosphonic acid.

Preferably, the phosphonic polymer comprises, or consists of:
(a) 85% to 95% by weight, relative to the total weight of monomers, of linear or branched $C_8$-$C_{22}$ alkyl (meth)acrylate;
(b) 5% to 15% by weight of vinylphosphonic acid monomer of formula (I) as defined previously.

The phosphonic polymer especially comprises, or consists of:
(a) 85% to 95% by weight, relative to the total weight of monomers, of linear or branched $C_8$-$C_{18}$ alkyl (meth)acrylate;
(b) 5% to 15% by weight of vinylphosphonic acid monomer of formula (I) as defined previously.

In particular, the phosphonic polymer comprises, or consists of:
(a) 85% to 95% by weight, relative to the total weight of monomers, of 2-ethylhexyl (meth)acrylate;
(b) 5% to 15% by weight of vinylphosphonic acid.

In particular, the phosphonic polymer comprises, or consists of:
(a) 85% to 95% by weight, relative to the total weight of monomers, of stearyl (meth)acrylate;
(b) 5% to 15% by weight of vinylphosphonic acid.

In particular, the phosphonic polymer comprises, or consists of:
(a) 85% to 95% by weight, relative to the total weight of monomers, of a mixture of 2-ethylhexyl (meth)acrylate and of stearyl (meth)acrylate;
(b) 5% to 15% by weight of vinylphosphonic acid.

Preferentially, the phosphonic polymer comprises, or consists of:
(a) 87% to 93% by weight, relative to the total weight of monomers, of linear or branched $C_8$-$C_{22}$ alkyl (meth)acrylate;
(b) 7% to 13% by weight of vinylphosphonic acid monomer of formula (I) as defined previously.

The phosphonic polymer especially comprises, or consists of:
(a) 87% to 93% by weight, relative to the total weight of monomers, of linear or branched $C_8$-$C_{18}$ alkyl (meth)acrylate;
(b) 7% to 13% by weight of vinylphosphonic acid monomer of formula (I) as defined previously.

In particular, the phosphonic polymer comprises, or consists of:
(a) 87% to 93% by weight, relative to the total weight of monomers, of 2-ethylhexyl (meth)acrylate;
(b) 7% to 13% by weight of vinylphosphonic acid.

In particular, the phosphonic polymer comprises, or consists of:
(a) 87% to 93% by weight, relative to the total weight of monomers, of stearyl (meth)acrylate;
(b) 7% to 13% by weight of vinylphosphonic acid.

In particular, the phosphonic polymer comprises, or consists of:
(a) 87% to 93% by weight, relative to the total weight of monomers, of a mixture of 2-ethylhexyl (meth)acrylate and of stearyl (meth)acrylate;
(b) 7% to 13% by weight of vinylphosphonic acid.

The phosphonic polymer may be chosen from the following copolymers:
2-ethylhexyl acrylate/vinylphosphonic acid
stearyl acrylate/vinylphosphonic acid
2-ethylhexyl acrylate/stearyl acrylate/vinylphosphonic acid
in the respective monomer contents described previously, and in particular:
the 2-ethylhexyl acrylate/vinylphosphonic acid copolymer (90/10 mass composition).

According to a second embodiment of the invention, the phosphonic polymer comprises, or consists of:
(a) 45% to 94.5% by weight, relative to the total weight of monomers, of linear or branched $C_8$-$C_{22}$ alkyl (meth)acrylate;
(b) 5% to 25% by weight of vinylphosphonic acid monomer of formula (I) as defined previously;
(c) 0.5% to 50% by weight of additional non-silicone monomer chosen from linear or branched $C_1$-$C_6$ alkyl (meth)acrylates or $C_6$-$C_{12}$ cycloalkyl (meth)acrylates.

The phosphonic polymer especially comprises, or consists of:
(a) 45% to 94.5% by weight, relative to the total weight of monomers, of linear or branched $C_8$-$C_{18}$ alkyl (meth)acrylate;
(b) 5% to 25% by weight of vinylphosphonic acid monomer of formula (I) as defined previously;
(c) 0.5% to 50% by weight of $C_6$-$C_{12}$ cycloalkyl (meth)acrylate.

In particular, the phosphonic polymer comprises, or consists of:
(a) 45% to 94.5% by weight, relative to the total weight of monomers, of 2-ethylhexyl (meth)acrylate;
(b) 5% to 25% by weight of vinylphosphonic acid;
(c) 0.5% to 50% by weight of isobornyl (meth)acrylate.

In particular, the phosphonic polymer comprises, or consists of:
(a) 45% to 94.5% by weight, relative to the total weight of monomers, of stearyl (meth)acrylate;
(b) 5% to 25% by weight of vinylphosphonic acid;
(c) 0.5% to 50% by weight of isobornyl (meth)acrylate.

In particular, the phosphonic polymer comprises, or consists of:
(a) 45% to 94.5% by weight, relative to the total weight of monomers, of a mixture of 2-ethylhexyl (meth)acrylate and of stearyl (meth)acrylate;
(b) 5% to 25% by weight of vinylphosphonic acid;
(c) 0.5% to 50% by weight of isobornyl (meth)acrylate.

Preferably, the phosphonic polymer comprises, or consists of:
(a) 45% to 90% by weight, relative to the total weight of monomers, of linear or branched $C_8$-$C_{22}$ alkyl (meth)acrylate;
(b) 5% to 25% by weight of vinylphosphonic acid monomer of formula (I) as defined previously;
(c) 5% to 50% by weight of additional non-silicone monomer chosen from linear or branched $C_1$-$C_6$ alkyl (meth)acrylates or $C_6$-$C_{12}$ cycloalkyl (meth)acrylates.

The phosphonic polymer especially comprises, or consists of:
(a) 45% to 90% by weight, relative to the total weight of monomers, of linear or branched $C_8$-$C_{18}$ alkyl (meth)acrylate;
(b) 5% to 25% by weight of vinylphosphonic acid monomer of formula (I) as defined previously;
(c) 5% to 50% by weight of $C_6$-$C_{12}$ cycloalkyl (meth)acrylate.

In particular, the phosphonic polymer comprises, or consists of:
(a) 45% to 90% by weight, relative to the total weight of monomers, of 2-ethylhexyl (meth)acrylate;
(b) 5% to 25% by weight of vinylphosphonic acid;
(c) 5% to 50% by weight of isobornyl (meth)acrylate.

In particular, the phosphonic polymer comprises, or consists of:
(a) 45% to 90% by weight, relative to the total weight of monomers, of stearyl (meth)acrylate;
(b) 5% to 25% by weight of vinylphosphonic acid;
(c) 5% to 50% by weight of isobornyl (meth)acrylate.

In particular, the phosphonic polymer comprises, or consists of:
(a) 45% to 90% by weight, relative to the total weight of monomers, of a mixture of 2-ethylhexyl (meth)acrylate and of stearyl (meth)acrylate;
(b) 5% to 25% by weight of vinylphosphonic acid;
(c) 5% to 50% by weight of isobornyl (meth)acrylate.

Preferentially, the phosphonic polymer comprises, or consists of:
(a) 55% to 80% by weight, relative to the total weight of monomers, of linear or branched $C_8$-$C_{22}$ alkyl (meth)acrylate;
(b) 5% to 15% by weight of vinylphosphonic acid monomer of formula (I) as defined previously;
(c) 15% to 40% by weight of additional non-silicone monomer chosen from linear or branched $C_1$-$C_6$ alkyl (meth)acrylates or $C_6$-$C_{12}$ cycloalkyl (meth)acrylates.

The phosphonic polymer especially comprises, or consists of:
(a) 55% to 80% by weight, relative to the total weight of monomers, of linear or branched $C_8$-$C_{18}$ alkyl (meth)acrylate;
(b) 5% to 15% by weight of vinylphosphonic acid monomer of formula (I) as defined previously;
(c) 15% to 40% by weight of $C_6$-$C_{12}$ cycloalkyl (meth)acrylate.

In particular, the phosphonic polymer comprises, or consists of:
(a) 55% to 80% by weight, relative to the total weight of monomers, of 2-ethylhexyl (meth)acrylate;
(b) 5% to 15% by weight of vinylphosphonic acid;
(c) 15% to 40% by weight of isobornyl (meth)acrylate.

In particular, the phosphonic polymer comprises, or consists of:
(a) 55% to 80% by weight, relative to the total weight of monomers, of stearyl (meth)acrylate;
(b) 5% to 15% by weight of vinylphosphonic acid;
(c) 15% to 40% by weight of isobornyl (meth)acrylate.

In particular, the phosphonic polymer comprises, or consists of:
(a) 55% to 80% by weight, relative to the total weight of monomers, of a mixture of 2-ethylhexyl (meth)acrylate and of stearyl (meth)acrylate;
(b) 5% to 15% by weight of vinylphosphonic acid;
(c) 15% to 40% by weight of isobornyl (meth)acrylate.

More preferentially, the phosphonic polymer comprises, or consists of:
(a) 58% to 73% by weight, relative to the total weight of monomers, of linear or branched $C_8$-$C_{22}$ alkyl (meth)acrylate;
(b) 7% to 13% by weight of vinylphosphonic acid monomer of formula (I) as defined previously;
(c) 20% to 35% by weight of additional non-silicone monomer chosen from linear or branched $C_1$-$C_6$ alkyl (meth)acrylates or $C_6$-$C_{12}$ cycloalkyl (meth)acrylates.

The phosphonic polymer especially comprises, or consists of:
(a) 58% to 73% by weight, relative to the total weight of monomers, of linear or branched $C_8$-$C_{18}$ alkyl (meth)acrylate;
(b) 7% to 13% by weight of vinylphosphonic acid monomer of formula (I) as defined previously;
(c) 20% to 35% by weight of $C_6$-$C_{12}$ cycloalkyl (meth)acrylate.

In particular, the phosphonic polymer comprises, or consists of:
(a) 58% to 73% by weight, relative to the total weight of monomers, of 2-ethylhexyl (meth)acrylate;
(b) 7% to 13% by weight of vinylphosphonic acid;
(c) 20% to 35% by weight of isobornyl (meth)acrylate.

In particular, the phosphonic polymer comprises, or consists of:
(a) 58% to 73% by weight, relative to the total weight of monomers, of stearyl (meth)acrylate;
(b) 7% to 13% by weight of vinylphosphonic acid;
(c) 20% to 35% by weight of isobornyl (meth)acrylate.

In particular, the phosphonic polymer comprises, or consists of:
(a) 58% to 73% by weight, relative to the total weight of monomers, of a mixture of 2-ethylhexyl (meth)acrylate and of stearyl (meth)acrylate;
(b) 7% to 13% by weight of vinylphosphonic acid;
(c) 20% to 35% by weight of isobornyl (meth)acrylate.

The phosphonic polymer may be chosen from the following copolymers:
2-ethylhexyl acrylate/vinylphosphonic acid/isobornyl (meth)acrylate stearyl acrylate/vinylphosphonic acid/isobornyl (meth)acrylate
2-ethylhexyl acrylate/stearyl acrylate/vinylphosphonic acid/isobornyl (meth)acrylate in the respective monomer contents described previously;
and in particular:
the 2-ethylhexyl acrylate/isobornyl acrylate/vinylphosphonic acid copolymer (70/20/10 mass composition).

According to a third embodiment of the invention, the phosphonic polymer comprises, or consists of:
(a) 45% to 94.5% by weight, relative to the total weight of monomers, of linear or branched $C_8$-$C_{22}$ alkyl (meth)acrylate;
(b) 5% to 25% by weight of vinylphosphonic acid monomer of formula (I) as defined previously;
(c) 0.5% to 50% by weight of silicone monomer (II) as described previously.

The phosphonic polymer especially comprises, or consists of:
(a) 45% to 94.5% by weight, relative to the total weight of monomers, of linear or branched $C_8$-$C_{18}$ alkyl (meth)acrylate;
(b) 5% to 25% by weight of vinylphosphonic acid monomer of formula (I) as defined previously;
(c) 0.5% to 50% by weight of silicone monomer (II) as described previously.

In particular, the phosphonic polymer comprises, or consists of:
(a) 45% to 94.5% by weight, relative to the total weight of monomers, of 2-ethylhexyl (meth)acrylate;
(b) 5% to 25% by weight of vinylphosphonic acid;
(c) 0.5% to 50% by weight of silicone monomer (II) as described previously.

In particular, the phosphonic polymer comprises, or consists of:
(a) 45% to 94.5% by weight, relative to the total weight of monomers, of sterile (meth)acrylate;
(b) 5% to 25% by weight of vinylphosphonic acid;
(c) 0.5% to 50% by weight of silicone monomer (II) as described previously.

In particular, the phosphonic polymer comprises, or consists of:
(a) 45% to 94.5% by weight, relative to the total weight of monomers, of a mixture of 2-ethylhexyl (meth)acrylate and of stearyl (meth)acrylate;
(b) 5% to 25% by weight of vinylphosphonic acid;
(c) 0.5% to 50% by weight of silicone monomer (II) as described previously.

Preferably, the phosphonic polymer comprises, or consists of:
(a) 45% to 90% by weight, relative to the total weight of monomers, of linear or branched $C_8$-$C_{22}$ alkyl (meth)acrylate;
(b) 5% to 25% by weight of vinylphosphonic acid monomer of formula (I) as defined previously;
(c) 5% to 50% by weight of silicone monomer (II) as described previously.

The phosphonic polymer especially comprises, or consists of:
(a) 45% to 90% by weight, relative to the total weight of monomers, of linear or branched $C_8$-$C_{18}$ alkyl (meth)acrylate;
(b) 5% to 25% by weight of vinylphosphonic acid monomer of formula (I) as defined previously;

(c) 5% to 50% by weight of silicone monomer (II) as described previously.

In particular, the phosphonic polymer comprises, or consists of:
(a) 45% to 90% by weight, relative to the total weight of monomers, of 2-ethylhexyl (meth)acrylate;
(b) 5% to 25% by weight of vinylphosphonic acid;
(c) 5% to 50% by weight of silicone monomer (II) as described previously.

In particular, the phosphonic polymer comprises, or consists of:
(a) 45% to 90% by weight, relative to the total weight of monomers, of stearyl (meth)acrylate;
(b) 5% to 25% by weight of vinylphosphonic acid;
(c) 5% to 50% by weight of silicone monomer (II) as described previously.

In particular, the phosphonic polymer comprises, or consists of:
(a) 45% to 90% by weight, relative to the total weight of monomers, of a mixture of 2-ethylhexyl (meth)acrylate and of stearyl (meth)acrylate;
(b) 5% to 25% by weight of vinylphosphonic acid;
(c) 5% to 50% by weight of silicone monomer (II) as described previously.

Preferentially, the phosphonic polymer comprises, or consists of:
(a) 55% to 80% by weight, relative to the total weight of monomers, of linear or branched $C_8$-$C_{22}$ alkyl (meth)acrylate;
(b) 5% to 15% by weight of vinylphosphonic acid monomer of formula (I) as defined previously;
(c) 15% to 40% by weight of silicone monomer (II) as described previously.

The phosphonic polymer especially comprises, or consists of:
(a) 55% to 80% by weight, relative to the total weight of monomers, of linear or branched $C_8$-$C_{18}$ alkyl (meth)acrylate;
(b) 5% to 15% by weight of vinylphosphonic acid monomer of formula (I) as defined previously;
(c) 15% to 40% by weight of silicone monomer (II) as described previously.

In particular, the phosphonic polymer comprises, or consists of:
(a) 55% to 80% by weight, relative to the total weight of monomers, of 2-ethylhexyl (meth)acrylate;
(b) 5% to 15% by weight of vinylphosphonic acid;
(c) 15% to 40% by weight of silicone monomer (II) as described previously.

In particular, the phosphonic polymer comprises, or consists of:
(a) 55% to 80% by weight, relative to the total weight of monomers, of stearyl (meth)acrylate;
(b) 5% to 15% by weight of vinylphosphonic acid;
(c) 15% to 40% by weight of silicone monomer (II) as described previously.

In particular, the phosphonic polymer comprises, or consists of:
(a) 55% to 80% by weight, relative to the total weight of monomers, of a mixture of 2-ethylhexyl (meth)acrylate and of stearyl (meth)acrylate;
(b) 5% to 15% by weight of vinylphosphonic acid;
(c) 15% to 40% by weight of silicone monomer (II) as described previously.

More preferentially, the phosphonic polymer comprises, or consists of:
(a) 58% to 73% by weight, relative to the total weight of monomers, of linear or branched $C_8$-$C_{22}$ alkyl (meth)acrylate;
(b) 7% to 13% by weight of vinylphosphonic acid monomer of formula (I) as defined previously;
(c) 20% to 35% by weight of silicone monomer (II) as described previously.

The phosphonic polymer especially comprises, or consists of:
(a) 58% to 73% by weight, relative to the total weight of monomers, of linear or branched $C_8$-$C_{18}$ alkyl (meth)acrylate;
(b) 7% to 13% by weight of vinylphosphonic acid monomer of formula (I) as defined previously;
(c) 20% to 35% by weight of silicone monomer (II) as described previously.

In particular, the phosphonic polymer comprises, or consists of:
(a) 58% to 73% by weight, relative to the total weight of monomers, of 2-ethylhexyl (meth)acrylate;
(b) 7% to 13% by weight of vinylphosphonic acid;
(c) 15% to 40% by weight of silicone monomer (II) as described previously.

In particular, the phosphonic polymer comprises, or consists of:
(a) 58% to 73% by weight, relative to the total weight of monomers, of stearyl (meth)acrylate;
(b) 7% to 13% by weight of vinylphosphonic acid;
(c) 15% to 40% by weight of silicone monomer (II) as described previously.

In particular, the phosphonic polymer comprises, or consists of:
(a) 58% to 73% by weight, relative to the total weight of monomers, of a mixture of 2-ethylhexyl (meth)acrylate and of stearyl (meth)acrylate;
(b) 7% to 13% by weight of vinylphosphonic acid;
(c) 15% to 40% by weight of silicone monomer (II) as described previously.

The ethylenic polymer may be chosen from the following copolymers:
2-ethylhexyl acrylate/vinylphosphonic acid/silicone monomer (II)
stearyl acrylate/vinylphosphonic acid/silicone monomer (II)
2-ethylhexyl acrylate/stearyl acrylate/vinylphosphonic acid/silicone monomer (II)
in the respective monomer contents described previously.

Polymers containing monomers (a) and (b) described previously are known.

Patent application US-A-2014/0 199 530 describes $C_{12}$-$C_{22}$ alkyl (meth)acrylate/vinylphosphonic acid copolymers with a phosphonic monomer/(meth)acrylate monomer weight ratio ranging from 0.1 to 10 as dispersants for printing inks.

U.S. Pat. No. 8,420,174 describes in Examples 13 and 14 terpolymers of acrylic acid/vinylphosphonic acid/lauryl acrylate with respective monomer mass ratios of 35/15/50 and 52.5/22.5/25 used for coating metal surfaces.

U.S. Pat. No. 5,009,670 describes in Example 10 a stearyl acrylate/vinylphosphonic acid copolymer in a 70/30 mass ratio used as fuel additive.

The phosphonic polymer as defined previously may be present in the composition used according to the invention in a content ranging from 0.1% to 40% by weight, relative to the total weight of the composition, preferably from 0.5% to 35% by weight of active material, preferentially ranging from 1% to 30% by weight, and more preferentially ranging from 10% to 30% by weight.

The Additional Component

The additional component used in the process according to the invention is especially an amine compound chosen from
- polyamine compounds containing one or more primary amine and/or secondary amine groups or alternatively amino alkoxysilanes. It may thus be chosen from amino alkoxysilanes, diamine compounds and triamine compounds.

According to a first embodiment of the invention, the polyamine compound is a compound comprising from 2 to 20 carbon atoms, in particular a non-polymeric compound. The term "non-polymeric compound" means a compound which is not directly obtained via a monomer polymerization reaction.

Polyamine

Polyamine compounds that may be mentioned include N-methyl-1,3-diaminopropane, N-propyl-1,3-diaminopropane, N-isopropyl-1,3-diaminopropane, N-cyclohexyl-1,3-diaminopropane, 2-(3-aminopropylamino)ethanol, 3-(2-aminoethyl)aminopropylamine, bis(3-aminopropyl)amine, methylbis(3-aminopropyl)amine, N-(3-aminopropyl)-1,4-diaminobutane, N,N-dimethyldipropylenetriamine, 1,2-bis(3-aminopropylamino)ethane, N,N'-bis(3-aminopropyl)-1,3-propanediamine, ethylenediamine, 1,3-propylenediamine, 1,4-butylenediamine, lysine, cystamine, xylenediamine, tris(2-aminoethyl)amine and spermidine. Preferably, the amine compound is chosen from ethylenediamine, 1,3-propylenediamine and 1,4-butylenediamine. Preferentially, the polyamine compound is ethylenediamine.

The polyamine compound may also be chosen from amine-based polymers, especially having a weight-average molecular weight ranging from 500 to 1 000 000, preferably ranging from 500 to 500 000, and preferentially ranging from 500 to 100 000.

As amine-based polymer, use may be made of poly(($C_2$-$C_5$)alkyleneimines), and in particular polyethyleneimines and polypropyleneimines, especially poly(ethyleneimine)s (for example the product sold under the reference 46,852-3 by the company Aldrich Chemical); poly(allylamine) (for example the product sold under the reference 47,913-6 by the company Aldrich Chemical); polyvinylamines and copolymers thereof, in particular with vinylamides; mention may in particular be made of vinylamine/vinylformamide copolymers such as those sold under the name Lupamin® 9030 by the company BASF; polyamino acids bearing $NH_2$ groups, such as polylysine, for example the product sold by the company JNC Corporation (formerly Chisso); aminodextran, such as the product sold by the company CarboMer Inc; amino polyvinyl alcohol, such as the product sold by the company CarboMer Inc, acrylamidopropylamine-based copolymers; chitosans;

polydimethylsiloxanes comprising primary amine groups at the chain end or on side chains, for example aminopropyl side or end groups, for instance those of formula (A) or (B) or (C):

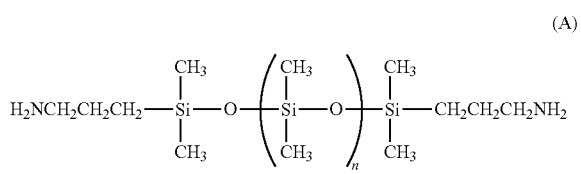

(A)

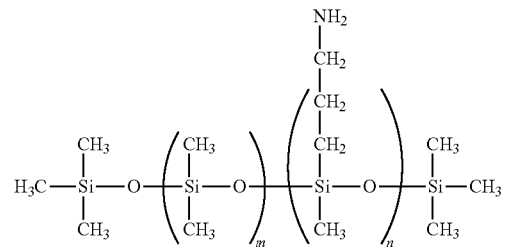

(B)

$H_2NCH_2CH_2CH_2$—$Si(CH_3)_2$—O—$[Si(CH_3)_2$—O$]_n$—$Si(CH_3)_2C_4H_9$ (C)

in formula (A): the value of n is such that the weight-average molecular weight of the silicone is between 500 and 55 000. As examples of aminosilicone (A), mention may be made of those sold under the names DMS-A11, DMS-A12, DMS-A15, DMS-A21, DMS-A31, DMS-A32 and DMS-A35 by the company Gelest, reference 481688 from Aldrich, in formula (B), the values of n and m are such that the weight-average molecular weight of the silicone is between 1000 and 55 000. As examples of silicone (B), mention may be made of those sold under the names AMS-132, AMS-152, AMS-162, AMS-163, AMS-191 and AMS-1203 by the company Gelest, in formula (C), the value of n is such that the weight-average molecular weight of the silicone is between 500 and 3000. As an example of silicone (C), mention may be made of those sold under the names MCR-A11 and MCR-A12 by the company Gelest;

amodimethicones of formula (D):

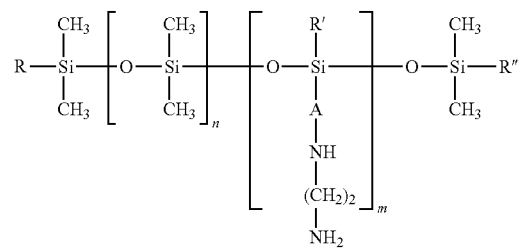

(D)

in which R, R' and R", which may be identical or different, each represent a $C_1$-$C_4$ alkyl or hydroxyl group, A represents a $C_3$ alkylene group and m and n are such that the weight-average molecular mass of the compound is between 5000 and 500 000 approximately. The polyether amines known especially under the reference Jeffamine® from the company Huntsman; and especially:

Polyethylene glycol and/or polypropylene glycol α,ω-diamines (bearing an amine function at the end of the chain), for instance the products sold under the names Jeffamine® D-230, D-400, D-2000, D-4000, ED-600, ED-9000, ED-2003.

Polytetrahydrofuran (or polytetramethylene glycol) α,ω-diamines, polybutadiene α,ω-diamines;

Polyamidoamine (PANAM) dendrimers bearing amine end functions.

Poly(meth)acrylates or poly(meth)acrylamides bearing primary or secondary amine side functions, such as poly(3-aminopropyl)methacrylamide or poly(2-aminoethyl) methacrylate;

As amine-based polymer, use is preferably made of polydimethylsiloxanes comprising primary amine groups at the chain end or on side chains.

Preferentially, polydimethylsiloxanes comprising aminopropyl end groups at the chain end are used.

Advantageously, the polyamine compounds used in the process according to the invention are chosen from ethylenediamine and polydimethylsiloxanes comprising primary amine groups at the chain end or on side chains.

Alkoxysilanes

The amine compound may also be chosen from amino alkoxysilanes, such as those of formula (III):

$$R'_1Si(OR'_2)_z(R'_3)_x \qquad (III)$$

in which:
- $R'_1$ is a linear or branched, saturated or unsaturated, cyclic or acyclic $C_1$-$C_6$ hydrocarbon-based chain substituted with a group chosen from the following groups:
  amine $NH_2$ or NHR with R=$C_1$-$C_4$ alkyl,
  an aryl or aryloxy group substituted with an amino group or with a $C_1$-$C_4$ aminoalkyl group,
  $R'_1$ possibly being interrupted in its chain with a heteroatom (O, S, NH) or a carbonyl group (CO), $R'_1$ being linked to the silicon atom directly via a carbon atom,
- $R'_2$ and $R'_3$, which may be identical or different, represent a linear or branched alkyl group comprising from 1 to 6 carbon atoms,
- z denotes an integer ranging from 1 to 3, and
- x denotes an integer ranging from 0 to 2, with z+x=3.

Preferably, $R'_2$ represents an alkyl group comprising from 1 to 4 carbon atoms.

Preferably, $R'_2$ represents a linear alkyl group, comprising from 1 to 4 carbon atoms.

Preferably, $R'_2$ represents an ethyl group.

Preferably, $R'_3$ represents an alkyl group comprising from 1 to 4 carbon atoms.

Preferably, $R'_3$ represents a linear alkyl group, comprising from 1 to 4 carbon atoms.

Preferably, $R'_3$ represents a methyl or ethyl group.

Preferably, $R'_1$ is an acyclic chain.

Preferably, $R'_1$ is a linear or branched, saturated or unsaturated $C_1$-$C_6$ hydrocarbon-based chain, substituted with an amine group $NH_2$ or NHR (R=$C_1$-$C_6$ alkyl, $C_3$-$C_6$ cycloalkyl or $C_6$ aromatic). Preferentially, $R'_1$ is a saturated linear $C_1$-$C_6$ hydrocarbon-based chain substituted with an amine group $NH_2$. More preferentially, $R'_1$ is a saturated linear $C_2$-$C_4$ hydrocarbon-based chain substituted with an amine group $NH_2$.

Preferably, $R'_1$ is a saturated linear $C_1$-$C_6$ hydrocarbon-based chain substituted with an amine group $NH_2$, $R'_2$ represents an alkyl group comprising from 1 to 4 carbon atoms, $R'_3$ represents an alkyl group comprising from 1 to 4 carbon atoms.

Preferably, z is equal to 3.

Preferably, the aminosilane of formula (III) is chosen from 3-aminopropyltriethoxysilane (APTES), 3-aminoethyltriethoxysilane (AETES), 3-aminopropylmethyldiethoxysilane, N-(2-aminoethyl)-3-aminopropyltriethoxysilane, 3-(m-aminophenoxy)propyltrimethoxysilane, p-aminophenyltrimethoxysilane and N-(2-aminoethylaminomethyl)phenethyltrimethoxysilane.

Preferably, the aminosilane (III) is chosen from 3-aminopropyltriethoxysilane (APTES), 3-aminoethyltriethoxysilane (AETES), 3-aminopropylmethyldiethoxysilane and N-(2-aminoethyl)-3-aminopropyltriethoxysilane.

Preferably, the aminosilane (III) is 3-aminopropyltriethoxysilane (APTES).

Preferably, the amine compound is chosen from 3-aminopropyltriethoxysilane (APTES), N-methyl-1,3-diaminopropane, N-propyl-1,3-diaminopropane, N-isopropyl-1,3-diaminopropane, N-cyclohexyl-1,3-diaminopropane, 2-(3-aminopropylamino)ethanol, 3-(2-aminoethyl)aminopropylamine, bis(3-aminopropyl)amine, methylbis(3-aminopropyl)amine, N-(3-aminopropyl)-1,4-diaminobutane, N,N-dimethyldipropylenetriamine, 1,2-bis(3-aminopropylamino)ethane, N,N'-bis(3-aminopropyl)-1,3-propanediamine, ethylenediamine and lysine.

Preferentially, the amine compounds used in the process according to the invention are chosen from polydimethylsiloxanes comprising primary amine groups at the chain end or on side chains, 3-aminopropyltriethoxysilane (APTES). More preferentially, polydimethylsiloxanes comprising aminopropyl end groups at the chain end, 3-aminopropyltriethoxysilane (APTES), are used.

Advantageously, the amine compound used in the process according to the invention is used in a mole ratio of amine group of the amine compound/phosphonic acid group of the phosphonic polymer ranging from 0.01 to 10, preferably ranging from 0.1 to 5, preferentially ranging from 0.1 to 2 and more preferentially ranging from 0.1 to 1.

On contact with the phosphonic polymer, the polyamine compound reacts with the phosphonic acid functions to form a crosslinked polymer, for example in the following manner:

Scheme I

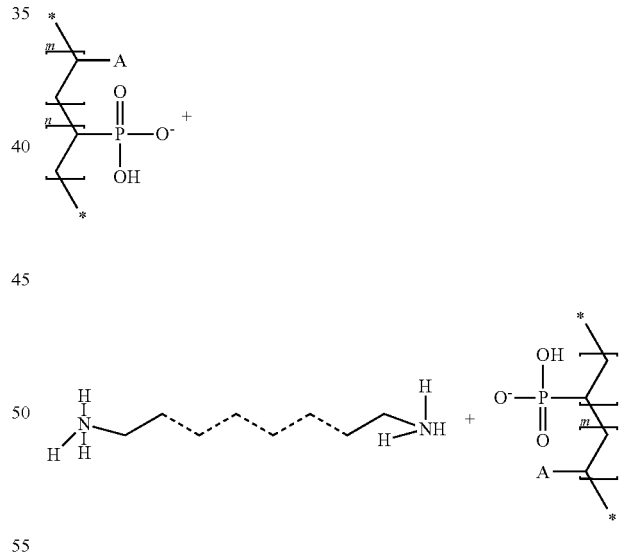

the unit bearing the group A symbolizing the unit derived from the fatty-chain ethylenic monomer.

Such a crosslinked polymer is novel and thus also forms the subject of the present invention.

The crosslinked polymer may thus be obtained by reacting said polyamine compound with the phosphonic polymer described previously. Some or all of the anhydride groups react with the NH or $NH_2$ group of the polyamine compound and form a unit bearing an amide group and a carboxylic acid group as described in scheme I.

On contact with the phosphonic polymer, in anhydrous medium, the amino alkoxysilane compound (III) reacts with the phosphonic acid functions to form a unit having the following formula:

Scheme II

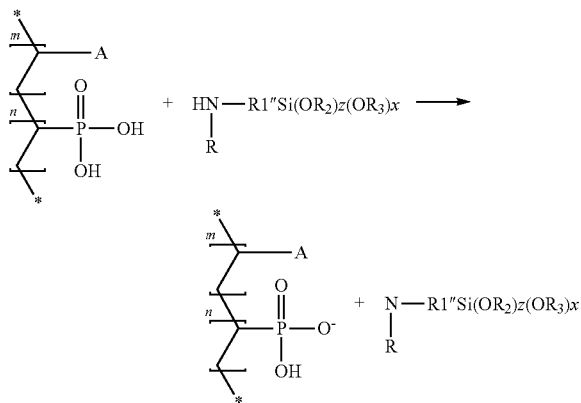

the unit bearing the group A symbolizing the unit derived from the fatty-chain ethylenic monomer.

Pigments

The composition that is useful in the process of the invention comprises at least one pigment. The term "pigment" means any pigment that gives colour to keratin materials. Their solubility in water at 25° C. and atmospheric pressure (760 mmHg) is less than 0.05% by weight, preferably less than 0.01%.

The pigments that may be used are chosen especially from the organic and/or mineral pigments known in the art, especially those described in Kirk-Othmer's chemical technology encyclopaedia and in Ullmann's industrial chemistry encyclopaedia.

These pigments may be in the form of powder or of pigmentary paste. They may be coated or uncoated.

The pigments may be chosen, for example, from mineral pigments, organic pigments, lakes, pigments with special effects such as nacres or glitter flakes, and mixtures thereof.

The pigment may be a mineral pigment. The term "mineral pigment" means any pigment that satisfies the definition in Ullmann's encyclopedia in the chapter on inorganic pigments. Among the mineral pigments that are useful in the present invention, mention may be made of iron oxides, chromium oxides, manganese violet, ultramarine blue, chromium hydrate, ferric blue and titanium oxide.

The pigment may be an organic pigment. The term "organic pigment" means any pigment that satisfies the definition in Ullmann's encyclopedia in the chapter on organic pigments. The organic pigment may be chosen especially from nitroso, nitro, azo, xanthene, quinoline, anthraquinone, phthalocyanin, metal-complex, isoindolinone, isoindoline, quinacridone, perinone, perylene, diketopyrrolopyrrole, thioindigo, dioxazine, triphenylmethane and quinophthalone compounds.

In particular, the white or coloured organic pigments may be chosen from carmine, carbon black, aniline black, azo yellow, quinacridone, phthalocyanin blue, sorghum red, the blue pigments codified in the Color Index under the references CI 42090, 69800, 69825, 73000, 74100 and 74160, the yellow pigments codified in the Color Index under the references CI 11680, 11710, 15985, 19140, 20040, 21100, 21108, 47000 and 47005, the green pigments codified in the Color Index under the references CI 61565, 61570 and 74260, the orange pigments codified in the Color Index under the references CI 11725, 15510, 45370 and 71105, the red pigments codified in the Color Index under the references CI 12085, 12120, 12370, 12420, 12490, 14700, 15525, 15580, 15620, 15630, 15800, 15850, 15865, 15880, 17200, 26100, 45380, 45410, 58000, 73360, 73915 and 75470, and the pigments obtained by oxidative polymerization of indole or phenolic derivatives as described in patent FR 2 679 771.

The pigments in accordance with the invention may also be in the form of composite pigments as described in patent EP 1 184 426. These composite pigments may be composed especially of particles comprising a mineral core, at least one binder for ensuring the binding of the organic pigments to the core, and at least one organic pigment at least partially covering the core.

The organic pigment may also be a lake. The term "lake" means dyes adsorbed onto insoluble particles, the assembly thus obtained remaining insoluble during use.

The inorganic substrates onto which the dyes are adsorbed are, for example, alumina, silica, calcium sodium borosilicate or calcium aluminium borosilicate, and aluminium.

Among the dyes, mention may be made of cochineal carmine. Mention may also be made of the dyes known under the following names: D&C Red 21 (01 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green (CI 61 570), D&C Yellow 10 (CI 77 002), D&C Green 3 (CI 42 053), D&C Blue 1 (CI 42 090).

An example of a lake that may be mentioned is the product known under the following name: D&C Red 7 (0115 850:1).

The pigment may also be a pigment with special effects. The term "pigments with special effects" means pigments that generally create a non-uniform coloured appearance (characterized by a certain shade, a certain vivacity and a certain lightness) that changes as a function of the conditions of observation (light, temperature, observation angles, etc.). They thus contrast with coloured pigments that afford a standard uniform opaque, semi-transparent or transparent shade.

Several types of pigments with special effects exist: those with a low refractive index, such as fluorescent, photochromic or thermochromic pigments, and those with a higher refractive index, such as nacres or glitter flakes.

Examples of pigments with special effects that may be mentioned include nacreous pigments such as titanium mica coated with an iron oxide, mica coated with an iron oxide, mica coated with bismuth oxychloride, titanium mica coated with chromium oxide, titanium mica coated with an organic dye especially of the abovementioned type, and also nacreous pigments based on bismuth oxychloride. They may also be mica particles at the surface of which are superposed at least two successive layers of metal oxides and/or of organic dyestuffs.

The nacres may more particularly have a yellow, pink, red, bronze, orange, brown, gold and/or coppery colour or tint.

By way of illustration of nacres that may be used in the context of the present invention, mention may especially be made of the gold-coloured nacres sold especially by the company Engelhard under the name Gold 222C (Cloisonne), Sparkle gold (Timica), Gold 4504 (Chromalite) and Monarch gold 233X (Cloisonne); the bronze nacres sold especially by the company Merck under the name Bronze fine (17384) (Colorona) and Bronze (17353) (Colorona), by the company Eckart under the name Prestige Bronze and by the company Engelhard under the name Super bronze (Cloisonne); the orange nacres sold especially by the company Engelhard under the name Orange 363C (Cloisonne) and Orange MCR 101 (Cosmica) and by the company Merck under the name Passion orange (Colorona) and Matte orange (17449) (Microna); the brown nacres sold especially by the company Engelhard under the name Nu-antique copper 340XB (Cloisonne) and Brown CL4509 (Chromalite); the nacres with a copper tint sold especially by the company Engelhard under the name Copper 340A (Timica) and by the company Eckart under the name Prestige Copper; the nacres with a red tint sold especially by the company Merck under the name Sienna fine (17386) (Colorona); the nacres with a yellow tint sold especially by the company Engelhard under the name Yellow (4502) (Chromalite); the red nacres with a gold tint sold especially by the company Engelhard under the name Sunstone G012 (Gemtone); the black nacres with a gold tint sold especially by the company Engelhard under the name Nu antique bronze 240 AB (Timica), the blue nacres sold especially by the company Merck under the name Matte blue (17433) (Microna), Dark Blue (117324) (Colorona), the white nacres with a silvery tint sold especially by the company Merck under the name Xirona Silver, and the golden-green pink-orange nacres sold especially by the company Merck under the name Indian summer (Xirona), and mixtures thereof.

In addition to nacres on a mica support, multilayer pigments based on synthetic substrates such as alumina, silica, sodium calcium borosilicate or calcium aluminium borosilicate, and aluminium, may be envisaged.

Mention may also be made of pigments with an interference effect that are not fixed onto a substrate, for instance liquid crystals (Helicones HC from Wacker), holographic interference flakes (Geometric Pigments or Spectra f/x from Spectratek). Pigments with special effects also comprise fluorescent pigments, whether these are substances that are fluorescent in daylight or that produce an ultraviolet fluorescence, phosphorescent pigments, photochromic pigments, thermochromic pigments and quantum dots, sold, for example, by the company Quantum Dots Corporation.

The variety of pigments that may be used in the present invention makes it possible to obtain a wide range of colours, and also particular optical effects such as metallic effects or interference effects.

The size of the pigment used in the cosmetic composition according to the present invention is generally between 10 nm and 200 μm, preferably between 20 nm and 80 μm and more preferentially between 30 nm and 50 μm.

The pigments may be dispersed in the product by means of a dispersant.

The dispersant serves to protect the dispersed particles against agglomeration or flocculation thereof. This dispersant may be a surfactant, an oligomer, a polymer or a mixture of several thereof, bearing one or more functionalities with strong affinity for the surface of the particles to be dispersed. In particular, they can physically or chemically attach to the surface of the pigments. These dispersants also contain at least one functional group that is compatible with or soluble in the continuous medium. In particular, 12-hydroxystearic acid esters in particular and $C_8$ to $C_{20}$ fatty acid esters of polyols such as glycerol or diglycerol are used, such as poly(12-hydroxystearic acid) stearate with a molecular weight of about 750 g/mol, such as the product sold under the name Solsperse 21 000 by the company Avecia, polyglyceryl-2 dipolyhydroxystearate (CTFA name) sold under the reference Dehymyls PGPH by the company Henkel, or polyhydroxystearic acid such as the product sold under the reference Arlacel P100 by the company Uniqema, and mixtures thereof.

As other dispersants that may be used in the compositions of the invention, mention may be made of quaternary ammonium derivatives of polycondensed fatty acids, for instance Solsperse 17 000 sold by the company Avecia, and polydimethylsiloxane/oxypropylene mixtures such as those sold by the company Dow Corning under the references DC2-5185 and DC2-5225 C.

The pigments used in the cosmetic composition according to the invention may be surface-treated with an organic agent.

Thus, the pigments that have been surface-treated beforehand, which are useful in the context of the invention, are pigments that have totally or partially undergone a surface treatment of chemical, electronic, electrochemical, mechanochemical or mechanical nature, with an organic agent such as those described especially in Cosmetics and Toiletries, February 1990, Vol. 105, pp. 53-64, before being dispersed in the composition in accordance with the invention. These organic agents may be chosen, for example, from amino acids; waxes, for example carnauba wax and beeswax; fatty acids, fatty alcohols and derivatives thereof, such as stearic acid, hydroxystearic acid, stearyl alcohol, hydroxystearyl alcohol and lauric acid and derivatives thereof; anionic surfactants; lecithins; sodium, potassium, magnesium, iron, titanium, zinc or aluminium salts of fatty acids, for example aluminium stearate or laurate; metal alkoxides; polysaccharides, for example chitosan, cellulose and derivatives thereof; polyethylene; (meth)acrylic polymers, for example polymethyl methacrylates; polymers and copolymers containing acrylate units; proteins; alkanolamines; silicone compounds, for example silicones, polydimethylsiloxanes, alkoxysilanes, alkylsilanes and siloxysilicates; organofluorine compounds, for example perfluoroalkyl ethers; fluorosilicone compounds.

The surface-treated pigments that are useful in the cosmetic composition according to the invention may also have been treated with a mixture of these compounds and/or may have undergone several surface treatments.

The surface-treated pigments that are useful in the context of the present invention may be prepared according to surface-treatment techniques that are well known to those skilled in the art, or may be commercially available in the required form.

Preferably, the surface-treated pigments are coated with an organic layer.

The organic agent with which the pigments are treated may be deposited on the pigments by evaporation of solvent, chemical reaction between the molecules of the surface agent or creation of a covalent bond between the surface agent and the pigments.

The surface treatment may thus be performed, for example, by chemical reaction of a surface agent with the surface of the pigments and creation of a covalent bond between the surface agent and the pigments or the fillers. This method is especially described in patent U.S. Pat. No. 4,578,266.

An organic agent covalently bonded to the pigments will preferably be used.

The agent for the surface treatment may represent from 0.1% to 50% by weight, preferably from 0.5% to 30% by weight and even more preferentially from 1% to 10% by weight relative to the total weight of the surface-treated pigments.

Preferably, the surface treatments of the pigments are chosen from the following treatments:
- a PEG-silicone treatment, for instance the AQ surface treatment sold by LCW;
- a chitosan treatment, for instance the CTS surface treatment sold by LCW;
- a triethoxycaprylylsilane treatment, for instance the AS surface treatment sold by LCW;
- a methicone treatment, for instance the SI surface treatment sold by LCW;
- a dimethicone treatment, for instance the Covasil 3.05 surface treatment sold by LCW;
- a dimethicone/trimethyl siloxysilicate treatment, for instance the Covasil 4.05 surface treatment sold by LCW;
- a lauroyllysine treatment, for instance the LL surface treatment sold by LCW;
- a lauroyllysine dimethicone treatment, for instance the LL/SI surface treatment sold by LCW;
- a magnesium myristate treatment, for instance the MM surface treatment sold by LCW;
- an aluminium dimyristate treatment, for instance the MI surface treatment sold by Myoshi;
- a perfluoropolymethylisopropyl ether treatment, for instance the FHC surface treatment sold by LCW;
- an isostearyl sebacate treatment, for instance the HS surface treatment sold by Miyoshi;
- a disodium stearoyl glutamate treatment, for instance the NAI surface treatment sold by Miyoshi;
- a dimethicone/disodium stearoyl glutamate treatment, for instance the SA/NAI surface treatment sold by Miyoshi;
- a perfluoroalkyl phosphate treatment, for instance the PF surface treatment sold by Daito;
- an acrylate/dimethicone copolymer and perfluoroalkyl phosphate treatment, for instance the FSA surface treatment sold by Daito;
- a polymethylhydrogen siloxane/perfluoroalkyl phosphate treatment, for instance the FS01 surface treatment sold by Daito;
- a lauryllysine/aluminium tristearate treatment, for instance the LL-StAI surface treatment sold by Daito;
- an octyltriethylsilane treatment, for instance the OTS surface treatment sold by Daito;
- an octyltriethylsilane/perfluoroalkyl phosphate treatment, for instance the FOTS surface treatment sold by Daito;
- an acrylate/dimethicone copolymer treatment, for instance the ASC surface treatment sold by Daito;
- an isopropyl titanium triisostearate treatment, for instance the ITT surface treatment sold by Daito;
- a microcrystalline cellulose and carboxymethylcellulose treatment, for instance the AC surface treatment sold by Daito;
- a cellulose treatment, for instance the C2 surface treatment sold by Daito;
- an acrylate copolymer treatment, for instance the APD surface treatment sold by Daito;
- a perfluoroalkyl phosphate/isopropyl titanium triisostearate treatment, such as the PF+ITT surface treatment sold by Daito.

The composition in accordance with the present invention may moreover comprise one or more surface-untreated pigments.

According to a particular embodiment of the invention, the pigment(s) are mineral pigments.

According to another particular embodiment of the invention, the pigment(s) are chosen from nacres.

The amount of pigments may range from 0.5% to 40% and preferably from 1% to 20%.

According to a first embodiment of the process according to the invention, an extemporaneous mixture of a composition comprising the phosphonic polymer and of an amine compound as described previously or of a composition containing same is applied to the hair, the mixture comprising at least one pigment.

According to a second embodiment of the process according to the invention, the composition comprising the phosphonic polymer is first applied to the keratin materials, and an amine compound as described previously or a composition containing same is then applied, one and/or the other of the compositions comprising at least one pigment. The pigment may also be applied using a separate composition.

According to a third embodiment of the process according to the invention, the amine compound as described previously, or a composition containing the same is first applied to the hair, and the cosmetic composition comprising the phosphonic polymer is then applied, one and/or the other of the compositions comprising at least one pigment. The pigment may also be applied using a separate composition.

Other Particular Additional Components

Other particular additional components may be used in the process according to the invention to contribute toward the film-forming properties of the polymer according to the invention. Such additional components are especially the salts of divalent or trivalent metal ions, clays and metal oxides described below.

The composition according to the invention may comprise salts of divalent or trivalent metal ions, chosen in particular from salts of ions derived from Al(III), Ca(II), Cu(II), Fe(II), Fe(III), Mg(II), Mn(II), Zn(II), and mixtures thereof. Ions derived from Ca(II), Mg(II) are preferred. The salts of these metal ions are well known, with, for example, anions such as gluconate, chloride, sulfate, hydroxide, acetate and stearate. For example, use may be made of the following salts: calcium gluconate, calcium chloride, magnesium chloride, copper chloride, magnesium gluconate, iron sulfate, iron gluconate, aluminium sulfate, sodium stearate.

Said salts of divalent or trivalent metal ions may be present in the composition according to the invention in a content ranging from 0.1% to 20% by weight, preferably from 0.1% to 15% by weight, relative to the total weight of the composition.

Alternatively, the salt of divalent or trivalent metal ions may be applied sequentially in the process according to the invention.

The composition according to the invention may comprise a clay.

Clays are products that are already well known per se, which are described, for example, in the publication Minéralogie des argiles [Mineralogy of Clays], S. Caillère, S. Hénin, M. Rautureau, 2nd Edition 1982, Masson, the teaching of which is included herein by way of reference.

Among the clays, examples that may be mentioned include clays of the smectite family, such as laponite and montmorillonite, of the kaolinite family, such as kaolinite, dickite, nacrite, optionally modified clays of the halloysite, dombassite, antigorite, benthierine, pyrophyllite, montmorillonite, beidellite, vermiculite, talc, stevensite, hectorite, bentonite, saponite, chlorite, sepiolite and illite family.

The clay(s) present in the composition of the invention may be natural or synthetic. Natural clay is a sedimentary rock composed to a large extent of specific minerals, silicates generally of aluminium. Kaolin is thus a natural clay.

The clays may also be chemically modified by various compounds, such as acrylic acids, polysaccharides (for example carboxymethylcellulose) or organic cations.

Preferably, in the context of the present invention, use is made of clays that are cosmetically compatible with and acceptable for human keratin materials.

According to a particular embodiment of the present invention, the clay used is chosen from kaolinite, montmorillonites, saponites, laponites, bentonites, and in particular hectorites, and illites. Use is even more particularly made of mixtures of clays, and natural clays.

Natural clays that may be mentioned include green clays, in particular rich in illite; clays rich in montmorillonite, known as fuller's earth, or such as bentonite or else white clays rich in kaolinite. Bentonites that may be mentioned in particular include those sold under the names Bentone 38 VCG, Bentone Gel CAO V, Bentone 27 V, Bentone Gel MIO V and Bentone Gel ISD V by the company Elementis.

Montmorillonites and smectites are hydrated aluminium and/or magnesium silicates. Examples that may be mentioned include the montmorillonite sold under the name Gel White H by the company Rockwood Additives, and the purified smectites sold under the name Veegum Granules by the company Vanderbilt. Mention may also be made of the montmorillonite sold under the name Kunipia G4 by the company Kunimine and the sepiolite Pangel S9 sold by the company Tolsa.

Examples of kaolinites that may be mentioned include the kaolins sold under the name Coslin C 100 by the company BASF Personal Care Ingredients or Kaolin Supreme by the company Imerys.

Talcs are hydrated magnesium silicates usually comprising aluminium silicate. The crystal structure of talc consists of repeated layers of a sandwich of brucite between layers of silica. Examples that may be mentioned include micronized magnesium silicate of particle size 5 microns sold under the name Micro Ace P3 by the company Nippon Talc or the talcs sold under the names Rose Talc and Talc SG-2000 by the company Nippon Talc, J 68 BC by the company US Cosmetics (Miyoshi), Lyzenac 00 and Luzenac Pharma M by the company Luzenac, and Talc JA-46R by the company Asada Milling.

As saponite, which belongs to the montmorillonite family, mention may be made of synthetic saponite, in particular the product sold by the company Kunimine under the name Sumecton®.

An example of a synthetic laponite that may be mentioned is the laponite XLG sold by the company Rockwood.

The clay may be present in the composition according to the invention in an amount ranging from 0.1% to 50% by weight, especially from 1% to 30% by weight and in particular from 1% to 20% by weight relative to the total weight of the composition.

The metal oxides may be chosen from titanium dioxide, iron oxides, zirconium oxides, zinc oxides, cerium oxides and chromium oxides. Iron oxides or titanium dioxide are preferably used.

The metal oxide may be present in the composition according to the invention in an amount ranging from 0.1% to 50% by weight, especially from 1% to 30% by weight and in particular from 1% to 20% by weight relative to the total weight of the composition.

Hydrocarbon-Based Oil

According to a preferred embodiment of the invention, the composition comprising the phosphonic polymer may contain a hydrocarbon-based oil.

The hydrocarbon-based oil is an oil that is liquid at room temperature (25° C.).

The term "hydrocarbon-based oil" means an oil formed essentially from, or even consisting of, carbon and hydrogen atoms, and optionally oxygen and nitrogen atoms, and not containing any silicon or fluorine atoms. It may contain alcohol, ester, ether, carboxylic acid, amine and/or amide groups.

The hydrocarbon-based oil may be volatile or non-volatile.

The hydrocarbon-based oil may be chosen from:

hydrocarbon-based oils containing from 8 to 14 carbon atoms, and especially:
- branched $C_8$-$C_{14}$ alkanes, for instance $C_8$-$C_{14}$ isoalkanes of petroleum origin (also known as isoparaffins), for instance isododecane (also known as 2,2,4,4,6-pentamethylheptane), isodecane and, for example, the oils sold under the trade name Isopar or Permethyl,
- linear alkanes, for instance n-dodecane (C12) and n-tetradecane (C14) sold by Sasol under the respective references Parafol 12-97 and Parafol 14-97, and also mixtures thereof, the undecane-tridecane mixture, the mixtures of n-undecane (C11) and of n-tridecane (C13) obtained in Examples 1 and 2 of patent application WO 2008/155 059 from the company Cognis, and mixtures thereof, short-chain esters (containing from 3 to 8 carbon atoms in total) such as ethyl acetate, methyl acetate, propyl acetate or n-butyl acetate, hydrocarbon-based oils of plant origin such as triglycerides consisting of fatty acid esters of glycerol, the fatty acids of which may have chain lengths varying from $C_4$ to $C_{24}$, these chains possibly being linear or branched, and saturated or unsaturated; these oils are especially heptanoic or octanoic acid triglycerides, or alternatively wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion-flower oil and musk rose oil; shea butter; or else caprylic/capric acid triglycerides, for instance those sold by the company Stéarineries Dubois or those sold under the names Miglyol 810®, 812° and 818° by the company Dynamit Nobel, synthetic ethers having from 10 to 40 carbon atoms;

linear or branched hydrocarbons of mineral or synthetic origin, such as petroleum jelly, polydecenes, hydrogenated polyisobutene such as Parleam®, squalane and liquid paraffins, and mixtures thereof, synthetic esters such as oils of formula $R_1COOR_2$ in which $R_1$ represents a linear or branched fatty acid residue containing from 1 to 40 carbon atoms and $R_2$ represents an, in particular, branched hydrocarbon-based chain containing from 1 to 40 carbon atoms, on the condition that $R_1+R_2 \geq 10$, for instance purcellin oil (cetostearyl octanoate), isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, alkyl or polyalkyl heptanoates, octanoates, decanoates or ricinoleates such as propylene glycol dioctanoate; hydroxylated esters such as isostearyl lactate, diisostearyl malate and 2-octyldodecyl lactate; polyol esters and pentaerythritol esters, fatty alcohols that are liquid at room temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol.

Advantageously, the hydrocarbon-based oil is apolar (thus formed solely from carbon and hydrogen atoms).

The hydrocarbon-based oil is preferably chosen from hydrocarbon-based oils containing from 8 to 14 carbon atoms, in particular the apolar oils described previously.

Preferentially, the hydrocarbon-based oil is isododecane.

Silicone Oils

The composition comprising the polymer may contain, in addition to the hydrocarbon-based oil, a silicone oil. The term "silicone oil" means an oil comprising at least one silicon atom and especially at least one Si—O group. The silicone oil may be volatile or non-volatile. The term "volatile oil" means an oil (or non-aqueous medium) that is capable of evaporating on contact with the skin in less than one hour, at room temperature and at atmospheric pressure. The volatile oil is a volatile cosmetic oil, which is liquid at room temperature, especially having a non-zero vapour pressure, at room temperature and atmospheric pressure, in particular having a vapour pressure ranging from 0.13 Pa to 40 000 Pa ($10^{-3}$ to 300 mmHg), preferably ranging from 1.3 Pa to 13 000 Pa (0.01 to 100 mmHg) and preferentially ranging from 1.3 Pa to 1,300 Pa (0.01 to 10 mmHg).

The term "non-volatile oil" means an oil with a vapour pressure of less than 0.13 Pa.

Volatile silicone oils that may be mentioned include volatile linear or cyclic silicone oils, especially those with a viscosity ≤8 centistokes (cSt) ($8 \times 10^{-6}$ m$^2$/s), and especially having from 2 to 10 silicon atoms and in particular from 2 to 7 silicon atoms, these silicones optionally comprising alkyl or alkoxy groups having from 1 to 10 carbon atoms. As volatile silicone oils that may be used in the invention, mention may be made especially of dimethicones with viscosities of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

As non-volatile silicone oils, mention may be made of linear or cyclic non-volatile polydimethylsiloxanes (PDMSs); polydimethylsiloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates.

Advantageously, the composition may comprise a hydrocarbon-based oil in a content ranging from 60% to 100% by weight relative to the total weight of the oils present in the composition and from 0 to 40% by weight of silicone oil. According to a preferred embodiment of the invention, the composition contains as oil only a hydrocarbon-based oil.

The composition according to the invention may comprise a cosmetic additive chosen from fragrances, preserving agents, fillers, UV-screening agents, oils, waxes, surfactants, moisturizers, vitamins, ceramides, antioxidants, free-radical scavengers, polymers, thickeners and dyestuffs.

The composition according to the invention may also comprise other dyestuffs such as liposoluble dyes or water-soluble dyes. This dyestuff may be present in a content ranging from 0.01% to 30% by weight, relative to the total weight of the composition.

The liposoluble dyes are, for example, Sudan Red, D&C Red 17, D&C Green 6, β-carotene, soybean oil, Sudan Brown, D&C Yellow 11, D&C Violet 2, D&C Orange 5, quinoline yellow and annatto. The water-soluble dyes are, for example, beetroot juice or methylene blue.

According to one embodiment, the composition according to the invention is an anhydrous composition. The term "anhydrous composition" means a composition containing less than 2% by weight of water, or even less than 0.5% of water, and is especially free of water. Where appropriate, such small amounts of water may especially be introduced by ingredients of the composition that may contain residual amounts thereof.

In particular, when the amine compound is an amino alkoxysilane (III) as defined previously, the composition containing it and the compositions used in the process are anhydrous compositions. Advantageously, these compositions also contain a $C_2$-$C_5$ monoalcohol such as ethanol or isopropanol, especially in a content ranging from 0.1% to 5% by weight, relative to the total weight of the composition.

The invention will now be described with reference to the examples that follow, which are given as non-limiting illustrations.

EXAMPLE 1: 2-ETHYLHEXYL ACRYLATE/VINYLPHOSPHONIC ACID COPOLYMER (90/10 MASS COMPOSITION) POLYMER 1

180 g of 2-ethylhexyl acrylate and 20 g of vinylphosphonic acid were placed in a jacketed 1-litre reactor equipped with a stirring anchor, followed by addition of 300 g of isododecane. The system was sparged with argon for 10 minutes, and 3 g of initiator tert-butyl peroxy-2-ethylhexanoate (Trigonox® 21S from AkzoNobel) were then added. The heating of the jacket was set at 90° C. for 7 hours at 150 rpm.

The medium was then diluted with 300 g of isododecane, and then concentrated by distillation to remove the unreacted monomers. A solution containing 50% by weight of the polymer in isododecane was finally obtained.

The polymer obtained has a number-average molecular weight (Mn) of 6800 and a weight-average molecular weight (Mw) of 138 000.

EXAMPLE 2: 2-ETHYLHEXYL ACRYLATE/ISOBORNYL ACRYLATE/VINYLPHOSPHONIC ACID COPOLYMER (70/20/10 MASS COMPOSITION) POLYMER 2

The polymer was prepared according to the procedure of Example 1, using 140 g of 2-ethylhexyl acrylate, 40 g of isobornyl acrylate and 20 g of vinylphosphonic acid. A solution containing 50% by weight of the polymer in isododecane was finally obtained.

The polymer obtained has a number-average molecular weight (Mn) of 4800 and a weight-average molecular weight (Mw) of 10 000.

EXAMPLE 3: 2-ETHYLHEXYL ACRYLATE/ISOBORNYL ACRYLATE/VINYLPHOSPHONIC ACID COPOLYMER (45/45/10 MASS COMPOSITION) POLYMER 3

The polymer was prepared according to the procedure of Example 1, using 90 g of 2-ethylhexyl acrylate, 90 g of isobornyl acrylate and 20 g of vinylphosphonic acid. A solution containing 40% by weight of the polymer in isododecane was finally obtained.

Preparation of the Dyeing Compositions

Invention: A dyeing composition was prepared from the solution of example 2 containing Polymer 2 in isododecane (15% active material), 6% of pigment (MICA (and) IRON OXIDES) and qs to 100% with Isododecane.

Comparison1: The following comparative composition was prepared with the same pigment used at the same concentration.

| Comparative composition 1 | Conc. |
|---|---|
| GLYCINE | 3% |
| PHENOXYETHANOL | 0.7% |
| DIVINYLDIMETHICONE/DIMETHICONE COPOLYMER (and) C12-13 PARETH-3 (and) C12-13 PARETH-23 (60% Active Material in an aqueous emulsion) | 8.3% |
| CAPRYLYL GLYCOL | 1% |
| MAGNESIUM ALUMINUM SILICATE | 1.1% |
| STYRENE/ACRYLATES/AMMONIUM METHACRYLATE COPOLYMER (and) SODIUM LAURETH SULFATE (and) CAPRYLYL GLYCOL (40% Active material in an aqueous emulsion 40%) | 21% |
| MICA (and) IRON OXIDES | 6% |
| water | q.s |

Comparison 2: A comparative composition was prepared from a solution containing as a polymere Terpolymer vinyl acetate/crotonic acid/vinylneodecanoate (supplier National Starch INCI VA/CROTONATES/VINYL NEODECANOATE COPOLYMER) (15% active material), 6% of pigment (MICA (and) IRON OXIDES) and qs 100% ethanol (ethanol was used to well solubilized the polymer in order to get an homogeneous, transparent composition).

Evaluation of the Color Resistance

These dyeing compositions were applied on locks of natural hair with 90% of white hair. The compositions were applied on dried hair and on wet hair. 0.5 g of the dyeing composition was applied on 1 g of hair lock. After 24 h hours, the locks were washed with water and dried. Then, the locks were shampooed several times.

The color resistance was visually evaluated on dried washed hair then after 1 shampoo, 3 shampoos and 5 shampoos according to a resistance evaluation scale ranging from 5 (high color resistance) to 1 (no color resistance).

The evaluation is summarized in the table below:

| | Application on | Water resistance | After 1 shampoo | After 3 shampoo | After 5 shampoo |
|---|---|---|---|---|---|
| Invention comp. 1 | Dried hair | 5 | 5 | 4 | 1 |
| | Wet hair | 5 | 5 | 4 | 1 |
| Comparative comp. 1 | Dried hair | 5 | 5 | 2 | 1 |
| | Wet hair | 5 | 5 | 2 | 1 |
| Comparative comp. 2 | Dried hair | 5 | 2 | 1 | 1 |

These examples show that the composition of the invention provides an improvement of the color resistance to shampoos. After 5 shampoos, the color is still acceptable whereas with the comparative compositions 1 or 2, the locks are no more colored.

Preparation of the Dyeing Compositions with an Additional Component

Invention 2: A dyeing composition was prepared from the solution of example 2 containing Polymer 2 in isododecane (15% active material), 6% of pigment (MICA (and) IRON OXIDES), a polyamine (Poly(dimethylsiloxane), bis(3-aminopropyl)terminated with Mn 25000 g/mol (PDMS-diNH$_2$) 15% as additional component and qs to 100% with isododecane.

Invention 3: A dyeing composition was prepared from the solution of example 2 containing Polymer 2 in isododecane (7.5% active material), 6% of pigment (MICA (and) IRON OXIDES), (3-aminopropyl)triethoxysilane (APTES) 7.5% and qs to 100% with isododecane Invention 4: A dyeing composition was prepared from the solution of example 3 containing Polymer 3 in isododecane (15% active material), 6% of pigment (MICA (and) IRON OXIDES) and qs to 100% with isododecane.

Invention 5: A dyeing composition was prepared from the solution of example 3 containing Polymer 3 in isododecane (11.2% active material), 6% of pigment (MICA (and) IRON OXIDES), a polyamine (Poly(dimethylsiloxane), bis(3-aminopropyl)terminated with Mn 25000 g/mol (PDMS-diNH$_2$) 3.8% as additional component and qs to 100% with isododecane.

The evaluation was conducted as previously described and the evaluation results are summarized in the table below:

| | Application on | Water resistance | After 1 shampoo | After 3 shampoo | After 5 shampoo |
|---|---|---|---|---|---|
| Invention comp. 2 | Dried hair | 5 | 5 | 5 | 3 |
| Invention comp. 3 | Dried hair | 5 | 5 | 3 | 1 |
| Invention comp. 4 | Dried hair | 5 | 5 | 3 | 1 |
| Invention comp. 5 | Dried hair | 5 | 5 | 5 | 5 |

These evaluation results show that the color resistance is maintained at least for 3 shampoos, and with invention 2 and 5 the color resistance is maintained even after 5 shampoos.

The invention claimed is:

1. A process for dyeing hair, comprising:
application to the hair of a composition comprising:
at least one pigment; and
at least one phosphonic polymer derived from the polymerization of:
(a) 45% to 95% by weight, relative to the total weight of monomers, of an ethylenic monomer bearing an at least C$_8$ linear or branched alkyl group;
(b) 5% to 25% by weight of vinylphosphonic acid monomer of formula (I);
(c) 0% to 50% by weight of additional monomer selected from the group consisting of:
(i) linear or branched C1-C6 alkyl (meth)acrylate or C6-C12 cycloalkyl (meth)acrylate non-silicone monomers;

(ii) polydimethylsiloxane silicone monomers bearing a mono(meth)acryloyloxy end group of formula (II) below:

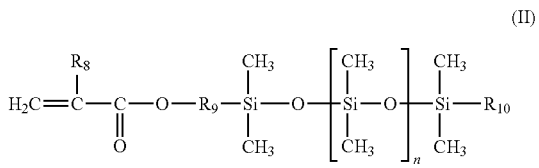
(II)

in which:
R8 denotes a hydrogen atom or a methyl group;
R9 denotes a linear or branched divalent hydrocarbon-based group containing from 1 to 10 carbon atoms and optionally containing one or two ether bonds —O—;
R10 denotes a linear or branched alkyl group containing from 1 to 10 carbon atoms;
n denotes an integer ranging from 1 to 300;
said vinylphosphonic acid monomer of formula (I) being:

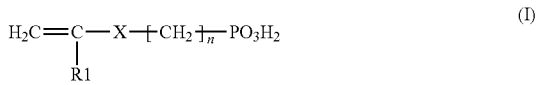
(I)

in which:
R1 denotes H or —CH3;
X denotes a covalent bond and n denotes an integer ranging from 0 to 14
or X denotes a —COO— group and n denotes an integer ranging from 2 to 6.

2. The process according to claim 1, wherein the ethylenic monomer bearing an at least $C_8$ linear or branched alkyl group is selected from the group consisting of:
a) linear or branched C8-C22 alkyl (meth)acrylates;
b) the (meth)acrylamides of formula

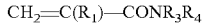

in which $R_1$ represents a hydrogen atom or a methyl radical, R3 represents a hydrogen atom or a linear or branched $C_1$-$C_{12}$ alkyl group, and $R_4$ represents a linear or branched $C_8$ to $C_{12}$ alkyl group;
c) vinyl esters of formula $R_5$—CO—O—CH═$CH_2$ in which $R_5$ represents a linear or branched $C_8$-$C_{22}$ alkyl group; and
d) ethers of formula $R_6$—O—CH═CH2 in which $R_6$ represents a linear or branched $C_8$-$C_{22}$ alkyl group.

3. The process according to claim 1, wherein the ethylenic monomer bearing an at least $C_8$ linear or branched alkyl group is selected from the group consisting of $C_8$-$C_{22}$ alkyl (meth)acrylates.

4. The process according to claim 1, the ethylenic monomer bearing an at least $C_8$ linear or branched alkyl group is selected from the group consisting of 2-ethylhexyl acrylate, 2-ethylhexyl methacrylate, lauryl acrylate, lauryl methacrylate, behenyl acrylate, behenyl methacrylate, stearyl acrylate and stearyl methacrylate.

5. The process according to claim 1, wherein the ethylenic monomer bearing an at least $C_8$ linear or branched alkyl group is present in said phosphonic polymer in a content ranging from 55% to 95% by weight, relative to the total weight of monomers.

6. The process according to claim 1, wherein, for the monomer (I) vinylphosphonic acid monomer of formula (I), X denotes a covalent bond and n is an integer ranging from 0 to 6, or X denotes a —COO— group and n is an integer ranging from 2 to 4.

7. The process according to claim 1, wherein, for the vinylphosphonic acid monomer of formula (I), R1=H and X denotes a covalent bond and n is an integer ranging from 0 to 4.

8. The process according to claim 1, wherein the vinylphosphonic acid monomer of formula (I) is selected from the group consisting of:
vinylphosphonic acid;
3-butenylphosphonic acid;
4-pentenylphosphonic acid;
10-undecenylphosphonic acid;
1 1-dodecenylphosphonic acid;
2-phosphonoethyl ester of 2-methyl-2-propenoic acid; and
2-phosphonoethyl ester of 2-propenoic acid.

9. The process according to claim 1, wherein said additional monomer is linear or branched C1-C6 alkyl (meth)acrylate or C6-C12 cycloalkyl (meth)acrylate non-silicone monomer and is selected from the group consisting of $C_6$-$C_{12}$ cycloalkyl (meth)acrylates.

10. The process according to claim 1, wherein said additional monomer is polydimethylsiloxane silicone monomer bearing a mono(meth)acryloyloxy end group of formula (II) and:
$R_8$ denotes a methyl group;
$R_9$ denotes a linear divalent hydrocarbon-based group containing from 2 to 4 carbon atoms;
$R_{10}$ denotes a linear or branched alkyl group, comprising from 2 to 8 carbon atoms; and
n denotes an integer ranging from 3 to 200.

11. The process according to claim 1, wherein said phosphonic polymer comprises an additional monomer present in a content ranging from 5% to 50% by weight, relative to the total weight of monomers.

12. The process according to claim 1, wherein said phosphonic polymer does not contain any additional monomer.

13. The process according to claim 1, wherein said phosphonic polymer comprises:
(a) 75% to 95% by weight, relative to the total weight of monomers, of the ethylenic monomer bearing an at least $C_8$ linear or branched alkyl group which is linear or branched $C_8$-$C_{22}$ alkyl (meth)acrylate; and
(b) 5% to 25% by weight of vinylphosphonic acid monomer of formula (I).

14. The process according to claim 1, wherein said phosphonic polymer is selected from the group consisting of the following copolymers:
2-ethylhexyl acrylate/vinylphosphonic acid
stearyl acrylate/vinylphosphonic acid; and
2-ethylhexyl acrylate/stearyl acrylate/vinylphosphonic acid.

15. The process according to claim 1, wherein said phosphonic polymer comprises:
(a) 45% to 94.5% by weight, relative to the total weight of monomers, of the ethylenic monomer bearing an at least $C_8$ linear or branched alkyl group which is linear or branched $C_8$-$C_{18}$ alkyl (meth)acrylate;
(b) 5% to 25% by weight of vinylphosphonic acid monomer of formula (I);
(c) 0.5% to 50% by weight of $C_6$-$C_{12}$ cycloalkyl (meth)acrylate non-silicone monomers.

16. The process according to claim 1, wherein the phosphonic polymer is selected from the group consisting of the following copolymers:

2-ethylhexyl acrylate/vinylphosphonic acid/isobornyl (meth)acrylate stearyl acrylate/vinylphosphonic acid/isobornyl(meth)acrylate; and 2-ethylhexyl acrylate/stearyl acrylate/vinylphosphonic acid/isobornyl (meth)acrylate.

17. The process according to claim 1, wherein the phosphonic polymer comprises:

(a) 45% to 94.5% by weight, relative to the total weight of monomers, of the ethylenic monomer bearing an at least $C_8$ linear or branched alkyl group which is linear or branched $C_8$-$C_{22}$ alkyl (meth)acrylate;

(b) 5% to 25% by weight of vinylphosphonic acid monomer of formula (I); and (c) 0.5% to 50% by weight of polydimethylsiloxane silicone monomers bearing a mono(meth)acryloyloxy end group of formula (II).

18. The process according to claim 1, wherein the phosphonic polymer is selected from the group consisting of the following copolymers:

2-ethylhexyl acrylate/vinylphosphonic acid/polydimethylsiloxane silicone monomers bearing a mono(meth)acryloyloxy end group of formula (II);

stearyl acrylate/vinylphosphonic polydimethylsiloxane silicone monomers bearing a mono(meth)acryloyloxy end group of formula (II);

2-ethylhexyl acrylate/stearyl acrylate/vinylphosphonic acid/polydimethylsiloxane silicone monomers bearing a mono(meth)acryloyloxy end group of formula (II).

19. The process according to claim 1, wherein the phosphonic polymer has a weight-average molecular weight ranging from 5000 to 1 000 000 g/mol.

20. The process according to claim 1, wherein:

either a composition derived from the mixing of (1) a composition comprising the phosphonic polymer and (2) an additional component or a composition containing an additional component, is applied to the hair, the composition derived from the mixing being anhydrous when the additional component is an amino alkoxysilane and the mixture applied to the hair containing at least one pigment;

or (1) a composition comprising the phosphonic polymer and (2) an additional component or a composition containing an additional component same, one and/or the other of the compositions comprising a pigment, are applied sequentially to the hair, the additional component being selected from the group consisting of:

(i) an amine compound chosen from polyamine compounds bearing several primary amine and/or secondary amine groups and amino alkoxysilanes, (ii) salts of divalent or trivalent metal ions, (iii) clays, and (iv) metal oxides, the compositions being anhydrous when the additional component is an amino alkoxysilane.

21. The process according to claim 20, wherein the additional component is a polyamine compound bearing several primary amine and/or secondary amine groups comprises from 2 to 20 carbon atoms.

22. The process according to claim 20, wherein the additional component is a polyamine compound bearing several primary amine and/or secondary amine groups is selected from the group consisting of N-methyl-1,3-diaminopropane, N-propyl-1,3-diaminopropane, N-isopropyl-1,3-diaminopropane, N-cyclohexyl-1,3-diaminopropane, 2-(3-aminopropylamino)ethanol, 3-(2-aminoethyl)aminopropylamine, bis(3-aminopropyl)amine, methylbis(3-aminopropyl)amine, N-(3-aminopropyl)-1,4-diaminobutane, N,N-dimethyldipropylenetriamine, 1,2-bis(3-aminopropylamino)ethane, N,N'-bis(3-aminopropyl)-1,3-propanediamine, ethylenediamine, 1,3-propylenedimaine, 1,4-butylenediamine, lysine, cystamine, xylenediamine, tris(2-aminoethyl)amine and spermidine.

23. The process according to claim 20, wherein the additional component is an amino alkoxysilane of formula (III)

in which:

R'$_1$ is a linear or branched, saturated or unsaturated, cyclic or acyclic $C_1$-$C_6$ hydrocarbon-based chain substituted with a group selected from the group consisting of the following groups:

amine $NH_2$ or NHR with R=$C_1$-$C_4$ alkyl, an aryl or aryloxy group substituted with an amino group or with a $C_1$-$C_4$ aminoalkyl group, R'$_1$ possibly being interrupted in its chain with a heteroatom (O, S, NH) or a carbonyl group (CO), R'$_1$ being linked to the silicon atom directly via a carbon atom, R'$_2$ and R'$_3$, which may be identical or different, represent a linear or branched alkyl group comprising from 1 to 6 carbon atoms, z denotes an integer ranging from 1 to 3, and x denotes an integer ranging from 0 to 2, with z+x=3.

24. The process according to claim 20, wherein the additional component is a polyamine compound bearing several primary amine and/or secondary amine groups chosen from polymers, having a weight-average molecular weight ranging from 500 to 1 000 000.

25. The process according to claim 24, wherein the polyamine compound is an amine-based polymer selected from the group consisting of poly(($C_2$-$C_5$)alkyleneimines); poly(allylamine); polyvinylamines and copolymers thereof; vinylamine/vinylformamide copolymers; polyamino acids bearing $NH_2$ groups; amino polyvinyl alcohol, acrylamidopropylamine-based copolymers; chitosans;

polydimethylsiloxanes comprising primary amine groups at the chain end or on side chains, including those of formula (A) or (B) or (C):

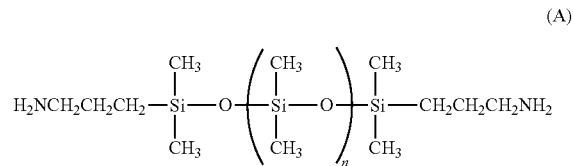

(B)

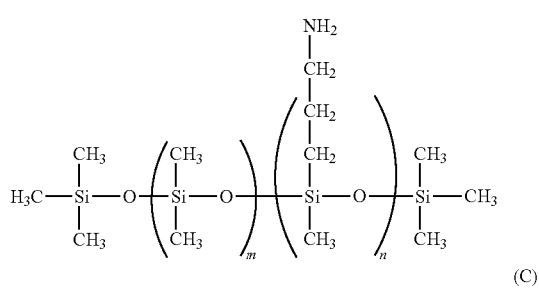

(C)

H₂NCH₂CH₂CH₂—Si(CH₃)₂—O—[Si(CH₃)₂—O]ₙ—Si(CH₃)₂C₄H₉ wherein:
in formula (A): the value of n is such that the weight-average molecular weight of the silicone is between 500 and 55 000;
in formula (B), the values of n and m are such that the weight-average molecular weight of the silicone is between 1000 and 55 000;
in formula (C), the value of n is such that the weight-average molecular weight of the silicone is between 500 and 3000;
amodimethicones of formula (D):

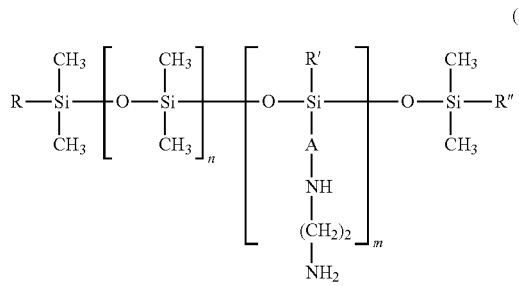

(D)

in which R, R' and R", which may be identical or different, each represent a $C_1$-$C_4$ alkyl or hydroxyl group, A represents a $C_3$ alkylene group and m and n are such that the weight-average molecular mass of the compound is between 5000 and 500 000;
polyetherdiamines; polytetrahydrofuran (or polytetramethylene glycol) α,ω-diamines and polybutadiene α,ω-diamines,
polyamidoamine dendrimers bearing amine end functions;
poly(meth)acrylates or poly(meth)acrylamides bearing primary or secondary amine side functions.

26. The process according to claim 20, wherein the additional component is an amine compound selected from the group consisting of polydimethylsiloxanes comprising primary amine groups at the chain end or on side chains and 3-aminopropyltriethoxysilane.

27. The process according to claim 20, wherein the amine compound is present in the composition in a mole ratio of amine group of the amine compound to acid group of the phosphonic polymer ranging from 0.01 to 10.

28. The process according to claim 20, wherein when the composition contains an amino alkoxysilane, it further comprises a $C_{2-05}$ monoalcohol in a content ranging from 0.1% to 5% by weight, relative to the total weight of the composition.

29. The process according to claim 20, wherein the additional component is a clay selected from the group consisting of clays of the smectite, kaolinite, halloysite, dombassite, antigorite, benthierine, pyrophyllite, montmorillonite, beidellite, vermiculite, talc, stevensite, hectorite, bentonite, saponite, chlorite, sepiolite and illite families.

30. The process according to claim 20, wherein the additional component is a salt of divalent or trivalent metal ions selected from the group consisting of salts of ions derived from Al(III), Ca(II), Cu(II), Fe(II), Fe(III), Mg(II), Mn(II), Zn(II) and mixtures thereof.

31. The process according to claim 20, wherein the additional component is a metal oxide selected from the group consisting of titanium dioxide, iron oxides, zirconium oxides, zinc oxides, cerium oxides and chromium oxides.

32. The process according to claim 20, wherein the mixing of the composition comprising the phosphonic polymer and the additional component or of the composition containing the additional component, is performed in a time of between 1 minute and 24 hours before its application to hair.

33. The process according to claim 1, wherein the composition further comprises an oil.

34. The process according to claim 1, in which the pigment(s) are present in the composition in an amount of between 0.5% and 40% by weight relative to the total weight of the composition.

35. A kit comprising a first composition comprising a phosphonic polymer as defined in claim 1 and a second composition comprising an additional component selected from the group consisting of:
(i) an amine compound chosen from polyamine compounds bearing several primary amine and/or secondary amine groups and amino alkoxysilanes,
(ii) salts of divalent or trivalent metal ions,
(iii) clays, and
(iv) metal oxides, and comprising a physiologically acceptable medium,
the first and second compositions each being packaged in a separate packaging assembly, the compositions being anhydrous when the additional compound is an amino alkoxysilane.

* * * * *

UNITED STATES PATENT AND TRADEMARK OFFICE
CERTIFICATE OF CORRECTION

PATENT NO. : 10,874,602 B2
APPLICATION NO. : 16/500615
DATED : December 29, 2020
INVENTOR(S) : Sandrine Chodorowski-Kimmes It is certified that error appears in the above-identified patent and that said Letters Patent is hereby corrected as shown below:

On the Title Page

Column 1, Item (51), under "Int. Cl.", Lines 1-4, delete "*A61Q 5/06*  (2006.01)" and insert -- *A61Q 5/10*  (2006.01) --, therefor.

|  |  |
|---|---|
| *A61Q 5/10* | (2006.01) |
| *A61K 8/81* | (2006.01) |
| *A61K 8/25* | (2006.01) |

In the Claims

In Column 28, Claim 1, Line 61, delete "(I);" and insert -- (I); and --, therefor.

In Column 28, Claim 1, Line 65, delete "C1-C6" and insert -- $C_1$-$C_6$ --, therefor.

In Column 28, Claim 1, Line 66, delete "C6-C12" and insert -- $C_6$-$C_{12}$ --, therefor.

In Column 29, Claim 1, Line 15, delete "R8" and insert -- $R_8$ --, therefor.

In Column 29, Claim 1, Line 16, delete "R9" and insert -- $R_9$ --, therefor.

In Column 29, Claim 1, Line 20, delete "R10" and insert -- $R_{10}$ --, therefor.

In Column 29, Claim 1, Line 31, delete "-CH3;" and insert -- -$CH_3$; --, therefor.

In Column 29, Claim 1, Line 33, delete "14" and insert -- 14; and --, therefor.

In Column 29, Claim 2, Line 39, delete "C8-C22" and insert -- $C_8$-$C_{22}$ --, therefor.

In Column 29, Claim 2, Line 40, delete "the (meth)acrylamides" and insert -- (meth)acrylamides --, therefor.

Signed and Sealed this
First Day of November, 2022

Katherine Kelly Vidal
*Director of the United States Patent and Trademark Office*

CERTIFICATE OF CORRECTION (continued)
U.S. Pat. No. 10,874,602 B2

In Column 29, Claim 2, Line 45, delete "R3" and insert -- $R_3$ --, therefor.

In Column 30, Claim 6, Line 2, delete "monomer (I) vinylphosphonic" and insert -- vinylphosphonic --, therefor.

In Column 30, Claim 9, Line 22, delete "C1-C6" and insert -- $C_1$-$C_6$ --, therefor.

In Column 30, Claim 9, Line 23, delete "C6-C12" and insert -- $C_6$-$C_{12}$ --, therefor.

In Column 30, Claim 15, Line 65, delete "(I);" and insert -- (I); and --, therefor.

In Column 31, Claim 18, Line 30, delete "(II);" and insert -- (II); and --, therefor.

In Column 31, Claim 20, Line 49, delete "component same," and insert -- component, --, therefor.

In Column 33, Claim 25, Lines 50-51, delete "functions;" and insert -- functions; and --, therefor.

In Column 34, Claim 28, Line 10, delete "$C_{2-05}$" and insert -- $C_2$-$C_5$ --, therefor.